(12) United States Patent
Horhota et al.

(10) Patent No.: US 6,228,394 B1
(45) Date of Patent: May 8, 2001

(54) SUPERCRITICAL FLUID EXTRACTION OF MOULD LUBRICANT FROM HARD SHELL CAPSULES

(75) Inventors: Stephen T. Horhota, Brookfield; Said Saim, New Milford, both of CT (US)

(73) Assignee: Boehringer Ingelheim Pharmaceuticals, Inc., Ridgefield, CT (US)

(*) Notice: Subject to any disclaimer, the term of this patent is extended or adjusted under 35 U.S.C. 154(b) by 0 days.

(21) Appl. No.: 09/157,267

(22) Filed: Sep. 21, 1998

Related U.S. Application Data

(60) Provisional application No. 60/062,099, filed on Oct. 14, 1997.

(51) Int. Cl.[7] ............................... A61K 9/64; A61K 9/48; F26B 3/00
(52) U.S. Cl. ........................... 424/456; 424/451; 34/329; 34/337; 34/341
(58) Field of Search ...................... 424/451, 456, 424/453, 454; 34/329, 337, 341

(56) References Cited

U.S. PATENT DOCUMENTS

| 5,198,115 | * | 3/1993 | Stalling et al. . |
| 5,287,632 | | 2/1994 | Heit et al. . |

FOREIGN PATENT DOCUMENTS

| 3545913A1 | 7/1986 | (DE) . |
| 0421577A2 | 4/1991 | (EP) . |
| WO 95/18834 | 7/1995 | (WO) . |
| WO 96/01105 | 1/1996 | (WO) . |

* cited by examiner

Primary Examiner—Thurman K. Page
Assistant Examiner—Brian K. Seidleck
(74) Attorney, Agent, or Firm—Robert P. Raymond; Alan R. Stempel; Mary-Ellen M. Devlin

(57) ABSTRACT

Hard shelled capsules and dry, powdered pharmaceutical formulations are treated with supercritical fluids to remove impurities such as mold lubricants and moisture.

21 Claims, 12 Drawing Sheets

Flow Diagram for SFE Unit

Flow Diagram for SFE Unit

Figure 1:
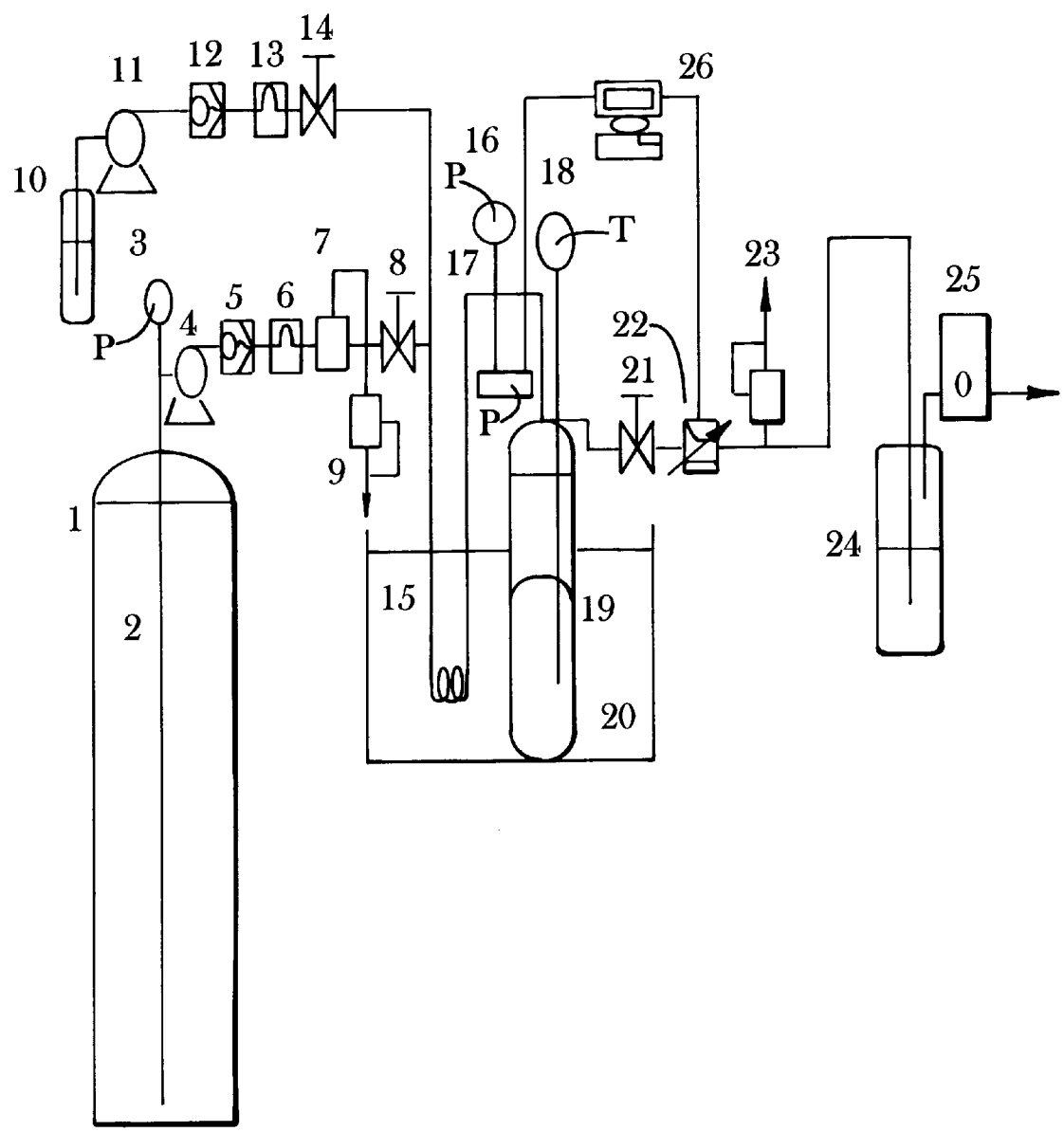

Temporal Change in Pressure in Dynamic SFE at 2,500 psig, 35°C.

Temporal Change in Pressure During Pressure Swing Extraction of Closed Capsules

Andersen particle Sizing Sampler Mark II with
Pre-Separator and Boehringer Inglehjeim Inhalator Andersen Sampler Stage Correspondence with the Human Repiratory System

ANDERSEN SAMPLERS-
Stimulates Human
Respiratory System

PRESEPARATOR
10 micrometers and above

STAGE 0
9.0 - 10

STAGE 1
5.8 - 9.0

STAGE 2
4.7 - 5.8    pharynx

STAGE 3    trachea and prmary
3.3 - 4.7    bronchi

STAGE 4    secondary
2.1 - 3.3    bronchi

STAGE 5    terminal
1.1 - 2.1    bronchi

STAGE 6
0.65 - 1.1    alveoli

STAGE 7
0.43 - 0.65    alveoli

Fractional Amount of Lubricant Extracted by
SFE Vs Time at 2,500 psig, 35°C

Fractional Amount of Lubricant Extracted in Two
Hours of Dynamic SFE Vs Pressure HPLC of Mixed Elution Solvent System
(Ethanol:Tetrahydrofuran-60:40,v/v)

HPLC of Lubricant in Capsules

HPLC of Lubricant Residue in Capsules
Following SFE

SEM of Untreated Capsule Inner Surface

SEM of SFE - Treated Capsule Inner Surface

Drug Retention in Control Capsules and SFE-Treated Capsules

Drug FPM Yielded by Control Capsules and SFE-Treated Capsules

Carrier Retention in Control Capsules and in SFE-Treated Capsules

Carrier FPM Yielded by Control Capsules and SFE-Treated Capsules

Reproducibility of Drug Retention in Control Capsules

Reproducibility of Drug Retention in SFE-Treated Capsules

Reproducibility of Drug Fine Particle Mass Yielded by Control Capsules

Reproducibility of Drug Fine Particle Mass Yielded by SFE-Treated Capsules

Large Scale SFE of Capsules: Drug Retention in SFE-Treated Capsules Vs Drug Retention in Corresponding Control Capsules

Fig. 22

Large Scale SFE : FPM of Drug Yielded by SFE Treated Capsules Vs FPM Yielded by Corresponding Control Capsules

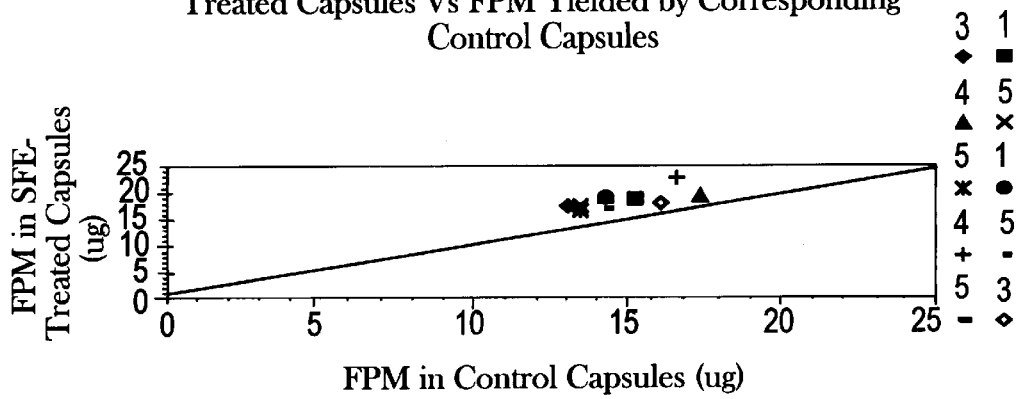

Fig. 23

Reproducibility of Drug Retention in Control Capsules Loaded with Drug Powder Using an Industrial Capsule Filling Machine

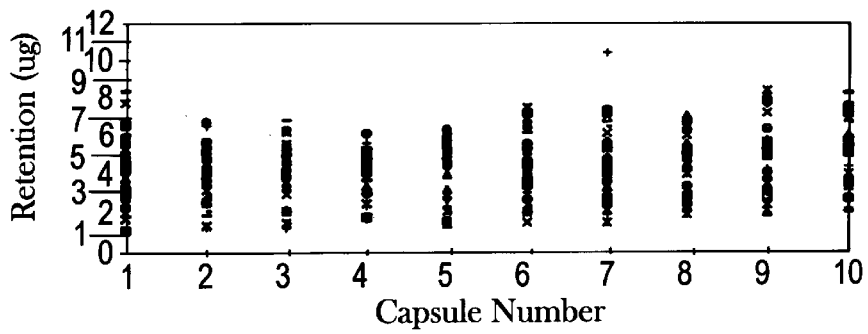

Fig. 24

Large Scale SFE of Capsules: Reproducibility of Drug Retention in SFE-Treated Capsules Loaded with Drug Powder Using an Industrial Filling Machine

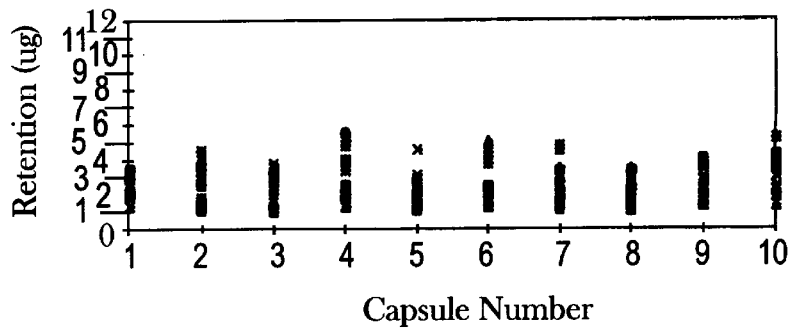

SUPERCRITICAL FLUID EXTRACTION OF MOULD LUBRICANT FROM HARD SHELL CAPSULES

The present application claims priority to U.S. Provisional Application No. 60/062,099, filed Oct. 14, 1997.

1. FIELD OF THE INVENTION

This invention is directed at methods for extracting undesirable materials present in capsules, which capsules are used to store and maintain powdered pharmaceutical formulations. In particular, the subject invention pertains to a method of treating capsules used to hold such powdered formulations to reduce the amount of undesirable materials such as molding lubricant or impurities that may be present in such capsules. Molding lubricant can cause retention of the powdered formulation, and result in inconsistent dosing of active drug. This invention also relates to a method for removing undesirable material from drug powder or from the material forming the capsule. Undesirable material in the capsules can be either moisture or impurities that, over a period of time, can come in contact with the capsule contents. Finally, the invention also relates to capsules treated according to the above method.

2. DESCRIPTION OF RELATED ART

Capsules are frequently used as a storage means for finely divided, pharmaceutical powders comprising active drug that is to be delivered to a patient via inhalation. For example, to avoid the use of propellant gases some of which (chloro-fluoro-carbons or CFCs) have been implicated with environmental damage (depletion of the ozone layer in the atmosphere), dry powder comprising the drug is placed in a capsule to be used with a dry powder inhaler (DPI). Generally, such devices cut or pierce the capsules comprising the dry powder prior to administration, and then the powder is inhaled by the patient.

The capsules usually consist of two (2) halves that are generally supplied by the capsule manufacturer in an assembled (closed) but not locked state. During capsule filling, the two halves are separated, filled with the pharmaceutical powder formulation comprising the active drug, and then closed and locked. Locked capsules are then inserted into the DPI.

Often, the capsule is a hard, gelatin capsule. Hard cellulose and plastic capsules suitable for storing pharmaceutical powders are also used. Such capsules are available from Capsugel (Belgium), Su-Heung (South Korea) and Elanco (U.S.A.), among other manufacturers.

Where the active drug in the powdered pharmaceutical formulation is to be delivered to the upper respiratory tract (i.e., intranasally), the particles of active drug should be about 20 to about 100 $\mu$m in size. Where administration of the active drug is to be to the lower respiratory tract (i.e., intrapulmonary) the particles of active drug are preferably less than about 5 $\mu$m in size.

Such sizes present handling problems (i.e., filling the capsules during manufacture), so the active drug is usually mixed with a coarse carrier. The carrier is typically glucose, lactose or mannitol. Additionally, many drugs used in inhalation therapy are given in small doses, i.e., less than about 250 micrograms, so the carrier can also serve as a bulking agent for such drugs. See, for example, U.S. Pat. No. 5,254,335. Moreover, the carrier can also be used to improve the aerodynamic flow of the formulation, and possibly to allow for the dispersion of the particles during inhalation.

Ipratropium bromide (I.B.) is an active drug that is typically administered via inhalation and marketed by Boehringer Ingelheim Pharmaceuticals, Inc. under the brand name ATROVENT®. It presents problems for use in DPIs since the amount of I.B. to be administered is very low (<50 micrograms). Accordingly, I.B. must be blended with a bulking agent such as lactose or glucose for administration via DPIs.

During manufacture of gelatin capsules the internal surfaces of such capsules become coated with mould release lubricants. This is because the manufacturing process for such capsules involves dipping mould pins into molten, capsule forming material, removing the pins from the bath of capsule forming material, and then allowing the capsule-forming material to harden on the pins. The hard capsule shells are then removed from the pins. In order to remove the capsule shells without damage, it is necessary to lubricate the mould pins. It is this lubricant which can coat the inside surface of the capsule. And it is this lubricant which can cause active drug retention in the capsule by the pharmaceutical formulation "sticking" to the walls of the capsule rather than being inhaled.

The problem of drug retention in capsules is compounded by the fact that the amount of lubricant in capsules varies not only from lot to lot but also within each lot from capsule to capsule. The lack of reproducibility in the fraction of drug that reaches the lungs, i.e. the inhalable fraction, may thus be due not only to the presence of lubricant, but also to the relatively large variance in the amount of lubricant in the capsules. None of these factors has proven easy to control during capsule manufacturing.

Additionally, as can well be imagined, the level of ambient humidity in addition to the moisture levels of the powdered pharmaceutical formulation, or capsules, can also affect consistency in dosing of active drug. Such can lead to retention of powdered formulation on the walls and surfaces of the capsules.

Lubricants have been shown to be responsible for most of the powder retention in hard gelatin capsules. Brown, S. (Boehringer Ingelheim Pharmaceuticals, Inc., Unpublished Results, 1994) and later Clark, A. R. and Gonda, I., (U.S. Pat. No. 5,641,510) have addressed this problem by extracting the lubricant material from the capsules using organic liquid solvents. Brown clearly demonstrated that washing the lubricant out of the capsules with an organic solvent leads to a marked reduction of retention. However, use of such solvents can introduce new impurities and solvent contamination, and do not allow for processing of the capsules in their closed state. Another possible solution is to limit the amount of oil that the capsule manufacturer use, so as to minimize adhesion of the powder to the internal surface of the capsule. This has proved not to be practical.

Accordingly, it is an object of the present invention to develop a method for reducing rentention of dry, powdered pharmaceutical formulation in capsules.

It is another object of the present invention to reduce the variation in amount of active drug provided in a dose from a DPI.

It is another object of the present invention to remove moisture or impurities from capsules and also powdered active drug formulations. Other objects and advantages of the present invention will become apparent to one of ordinary skill in the art.

SUMMARY OF THE INVENTION

The current invention addresses the problems of retention of powdered formulation in the capsules in a simple and non-intrusive way. It provides a new and novel means for minimizing the amount of powder retained in the capsules following inhalation, thereby increasing the amount of active drug reaching the lungs of the patient, while improving its reproducibility. This invention also provides a means for controlling the moisture level of the capsules.

Use of supercritical fluids (SCFs) to extract lubricant material from capsules provides great flexibility in processing. The amount and nature of the unextracted fraction of the lubricant material left in the capsules can be affected by either changing the extraction time, pressure, temperature, and/or flow rate of the pure SCF, or by adding small amounts of an organic solvent to the pure SCF to increase or decrease the solvent strength of the SCF mixture. Contrary to extraction with liquid solvents, the present methods also allows for extraction of capsules in either their open, closed or locked state with no apparent physical change. The ability to extract closed capsules is important since capsules are provided by the capsule manufacturer in their closed state, and are fed into the capsule filling machine in a closed state, and it would therefore be preferable to be able to extract them in this state without causing them to open.

It has been unexpectedly discovered that SCFs can be used in lieu of organic solvents, aqueous solvents, or solid substances to treat the capsules so as to achieve a lower retention of drug and carrier in the capsule following inhalation, and concomitantly achieve higher and more consistent drug delivery from DPIs. SCFs are found to selectively extract the fraction of the lubricant material that is responsible for most of the drug retention from either open, closed or locked capsules. In addition, it has been discovered that SCFs can also be used to remove trace impurities and moisture from capsules, drug and carrier particles in order to achieve more consistent surface properties, with no observed damage to either the capsule or the formulation. It has been found that selective extraction of lubricant material has a surprisingly positive effect on drug retention in the capsule and fine particle mass (particles $<5.8\ \mu m$) in a cascade impactor used to determine the aerodynamic particle size distribution of the powder and thereby approximate the amount of drug that will reach the lungs of the patient. It is found that extraction with SCFs provides a means to remove most of the adhesive fraction from the lubricant material, leaving nearly-solid to completely solid residue on the internal surface of the capsules. This novel method thus provides a means for removing the components of the lubricant material which are in large part responsible for drug retention in the capsule, and for making the surface of the capsules more uniform and more consistent by leaving an essentially solid residue on the internal surface of the capsules. The same technique is found to provide a means for reducing the moisture content of the capsules to a level that is similar to the desired level just prior to packaging of the DPI.

BRIEF DESCRIPTION OF THE DRAWINGS

FIG. 1 is a schematic diagram of a unit that can be used to practice the method of the present invention.

FIG. 2 is a graph showing the temporal change in pressure during a typical dynamic supercritical fluid extraction (SFE) experiment.

FIG. 3 is a graph showing the temporal change in pressure in a typical pressure swing SFE of capsules experiment FIG. 4 is a schematic diagram of the Andersen particle sizing sampler Mark II with pre-separator and an inhalator.

FIG. 5 is a schematic diagram of Andersen sampler stage correspondence with the human respiratory system.

FIG. 6 is a graph of the amount of lubricant extracted by SPE Vs time

FIG. 7 is a graph of the amount of lubricant extracted in two hours of dynamic SFE Vs Pressure FIG. 8 is the HPLC chromatogram of the mixture elution solvent system FIG. 9 is an HPLC chromatogram of lubricant in capsules FIG. 10 is an HPLC chromatogram of lubricant residue in capsules following SFE of capsules according to this invention.

FIG. 11 is a scanning electron microscopy (SEM) micrograph of an inner surface of a control capsule.

FIG. 12 is an SEM micrograph of an inner surface of an SFE-treated capsule according to the present invention.

FIG. 13 is a chart showing the difference between drug retention in control capsules and drug retention in SFE-treated capsules according to the present invention.

FIG. 14 is a chart showing the difference between drug fine particle mass (FPM) yielded by control capsules and drug FPM yielded by SFE-treated capsules according to the present invention.

FIG. 15 is a chart showing the difference between carrier retention in control capsules and carrier retention in SFE-treated capsules according to the present invention.

FIG. 16 is a chart showing the difference between carrier FPM yielded by control capsules and carrier FPM yielded by SFE-treated capsules according to the present invention.

FIG. 17 is a chart illustrating the reproducibility of drug retention in control capsules.

FIG. 18 is a chart illustrating the reproducibility of drug retention in SFE-treated capsules according to the present invention.

FIG. 19 is a chart illustrating the reproducibility of drug FPM yielded by control capsules.

FIG. 20 is a chart illustrating the reproducibility of drug FPM yielded by SFE-treated capsules according to the present invention.

FIG. 21 is a chart that shows the difference in drug retention in control capsules and drug retention in extracted capsules at large scale according to the present invention.

FIG. 22 is a chart that shows the difference in drug FPM yielded by control capsules and FPM yielded by extracted capsules at large scale according to the present invention.

FIG. 23 is a chart illustrating the reproducibility of drug retention in control capsules.

FIG. 24 illustrating the reproducibility of drug retention in SFE-treated capsules at large scale according to this invention.

DETAILED DESCRIPTION OF THE INVENTION

The word "capsule" when used herein refers to a telescoping capsule consisting of two parts: a body and a cap of slightly larger diameter which fits snugly over its open end. The powdered pharmaceutical formulation with active drug is placed inside the space defined by the inside walls of the body and cap. The capsule is generally suitable for storing a pharmaceutical compound which is to be administered to the patient in the form of an aerosol. The capsule is "hard" which means that it is sufficiently rigid to enable the pharmaceutical powder to be stored therein, yet is able to be cut or pierced prior to use, to allow administration of the pharmaceutical powder to the patient.

Examples of suitable capsules include hard gelatin, cellulose and plastic capsules, which are made principally of gelatin blends, cellulose and plastic materials, respectively, but may contain dyes, opaquing agents, plasticizers and preservatives, for example.

The capsules are generally formed by dip-molding a film-forming solution. In the manufacture of such capsules, mould-release lubricants are used to facilitate the removal of the mould pins from the capsule-forming core, and lubricant is thus left on the inside surface of the capsule halves.

By "lubricant" is meant a material capable of reducing friction between the mould pins and the inside surface of the formed capsule. The lubricant is compatible with the capsule (i.e., should not degrade the capsule), facilitates removal of the capsule from the mould pins and is pharmaceutically acceptable (i.e., non-toxic). While the lubricant can be a single lubricative compound, it may also be a "lubricant composition" having one or more lubricative compounds and, optionally, other additives or diluents present therein.

Many suitable lubricants are available and are used in capsule manufacture. Examples of possible lubricants include: silicone oil; sodium or magnesium lauryl sulfate; fatty acids (e.g., stearic and lauric acid); stearates (e.g., magnesium, aluminum or calcium stearate); boric acid; vegetable oils; mineral oils (e.g. paraffin); phospholipids (e.g., lecithin); polyethylene glycols; sodium benzoate; and mixtures of the above. Often, other components are present in the lubricant. For example, calcium soap may be dispersed in the oil lubricant. Sometimes, the lubricant is dissolved in petroleum, for example. Such lubricant compositions are well known in the art and are meant to be encompassed by the term "lubricant".

The term "pharmaceutical powder" when used throughout this application refers to a powder comprising at least one active drug and, optionally, a pharmaceutically acceptable carrier or excipient. The pharmaceutical powder is generally administered to the respiratory tract of the patient through inhalation. The invention is especially useful for low dosage drugs. The average size of the particles of the pharmaceutical powder containing the therapeutic agent is preferably in the range 0.1 to 20 micrometers, more preferably 1 to 6 micrometers. Typically, at least 50% of the particles will be of a size which falls within these ranges.

Examples of active drugs which can be administered to the respiratory tract of a patient include agents with an anti-histamine and anti-allergic action such as sodium cromoglycate, beta-agonists, anticholinergics such as ipratropium bromide, tiotropium bromide, oxytropium bromide and thiazinamide chloride, sympathomimetic amines such as terbutaline, albuterol, clenbuterol, pirbuterol, reproterol, procaterol and fenoterol, steroids especially corticosteroids such as beclomethasone dipropionate, and mucolytics such as ambroxol. Polypeptides may also be the active drug, such as growth hormones, parathyroid hormone, thyroid stimulating hormone, anti-clotting factors and lung surfactants, among others. Generally, the polypeptide is a peptide or protein having more than about ten amino acids.

Examples of other active drugs which might usefully be incorporated into the hard gelatin capsule include hypnotics, sedatives, tranquilizers, anti-inflammatory agents, antihistamines, anti-tussives, anti-convulsants, muscle-relaxants, anti-spasmodics, cardiovascular gents, anti-bacterials such as pentamidine, antibiotics and hypoglycemic agents.

Generally, because of handling and dosages involved, as discussed hereinabove, the pharmaceutical powder includes a pharmaceutically acceptable carrier or excipient. For example, a physical blend of the active drug and the carrier can be made, with the fine active drug particles adhering to the relatively larger carrier particle. Alternatively, a uniform mixture of the active drug particles and the excipient can form the pharmaceutical powder. Examples of pharmaceutically acceptable carrier or excipients include, but are not limited to,, salt compounds (e.g., sodium chloride) or sugar compounds (e.g., glucose, fructose, lactose, mannitol, trehalose and sucrose). The sugar compounds may be crystalline, amorphous or mixtures thereof.

Other compounds can be present in the pharmaceutical powder where required or desired. For example, a bronchodilator (e.g., isoprenaline, rimiterol, ephedrine, ibuterol, isoetharine, fenoterol, carbuterol, clenbuterol or pharmaceutically acceptable salts thereof) or a coloring or flavoring agent or preservatives, such as those which are conventionally incorporated into dry powder inhalant compositions, may be present in the pharmaceutical powder.

A "supercritical fluid" (SCF) is a substance or a mixture of substances above its critical temperature and critical pressure. The term "supercritical fluid" is also used to refer to a fluid that is gaseous under atmospheric conditions and that has a moderate, critical temperature (i.e., less than 200° C.). A SCF such as carbon dioxide above its critical temperature and pressure (31° C., 1,070 psig) behaves like a compressed gas. The density, and in general, the solvent power of a SCF increases with an increase in pressure to a point where it approaches that of many organic solvents. However, because of its gaseous nature, a SCF is characterized by a higher diffusivity than liquids, and therefore has the ability to more rapidly transport extracted material from a matrix such as capsules to the bulk $CO_2$ phase. Contrary to extraction with liquids, a SCF is also easily vented out of an extractor, leaving no residue on the extracted matrix (i.e., the capsules) and no need for further drying. A wealth of information on the properties of SCFs, including the solubility of lipidic material similar to lubricants used in capsule manufacture in SCFs is available in the technical literature (McHugh, M. And Krukonis, V. "Supercritical Fluid Extraction, Principles and Practice, $2^{nd}$ Ed., Butterworths, 1993).

A SCF such as $CO_2$ has a special affinity for lipidic material such as lubricants used for capsule mould release, and is therefore particularly suitable for such an application. However, SCFs such as $CO_2$ are more selective in what they extract than most organic solvents. Hence, $CO_2$-insoluble lubricant components that are generally solid and dry are not extracted, and are left on the internal surface of the capsules. This compares to the method of extracting lubricant material with organic solvents, which have the tendency to extract nearly all the lubricant and to leave residual solvent contamination in the capsule. The current invention can also be used to extract lubricants that are fully soluble in the SCF of choice or at operating conditions of temperature, pressure, flow rate, extraction time and SCF modifier such that all the lubricant is extracted, without leaving any residue. It should be noted that, according to this invention, it is also possible to devise a composition of lubricant material such that, after subjection of the capsules to SFE, any residue would be of optimal composition and texture to yield the desired, minimum retention in the capsules. The residue may also act as a barrier to moisture diffusion into the contents of the capsules (i.e., active drug and excipient or carrier material). This invention can also be used to extract solvent or other soluble material used in the formulation of a drug product, to leave a dry product in the capsule.

Another distinct feature of this invention is that, unlike liquid solvents, SCFs can be used to extract lubricants from empty open capsules, empty closed capsules or filled locked capsules without leaving any solvent contamination.

A SCF such as $CO_2$ also does not alter the color, appearance or physical properties of the capsules. In particular, under certain conditions, $CO_2$ does not extract any substantial amount of active drug, or the bulking agents, such as lactose, so that trace level impurities may be extracted from the surface of the particles without altering the formulation. Moreover, $CO_2$ is found to provide a means for drying capsules to a level that is just sufficient to minimize moisture effects on drug retention.

This invention has further determined that selective extraction of some lubricant compounds provides a simpler, more efficient, less intrusive and more feasible method for minimizing the effect of lubricant material than any other known method. It is found that SCF extraction (SFE) produces capsules that exhibit a lower strength of interaction with the drug and carrier particles than un-extracted capsules. In addition, this method allows for drying the capsules and drug and carrier particles to a desired level, and for removing trace contamination from the surfaces of drug and carrier particles.

The present invention provides great flexibility in processing. The amount and nature of the unextracted fraction of the lubricant material left in the capsules can be affected by either changing the extraction time, pressure, temperature, or flow rate of the SCF, or by adding small amounts of an organic solvent to the SCF to increase or decrease the solvent strength of the SCF mixture. Alternatively, $CO_2$, in its subcritical form (gas or liquid), may also be used to extract the lubricant material.

The present invention is thus a novel method for:
1. extraction of lubricant material from capsules;
2. extraction of undesirable material from capsules and their content;
3. drying the capsules to a desired moisture, and brittleness level; and
4. removing impurities or undesirable material from drug and carried particles.

This technique, contrary to the previously mentioned techniques, is non-intrusive (does not introduce any new solid substance, liquid substance or impurity), does not leave any measurable amount of residue, and does not require any further drying. The process is simple to design and scale up, and can be completed in a few hours. It leaves the capsules with essentially no damage and no change in their appearance or color.

The present invention makes use of non-intrusive SCFs for treating the surfaces of capsules in such a way as to dramatically reduce the amount of drug or carrier retained in the capsules following inhalation and concomitantly appreciably enhancing the amount of drug delivered and the reproducibility of dosages from a DPI. The present invention is simpler to implement than previous techniques such as organic solvent extraction, and can be used to treat: (1) open capsules for the purpose of extracting the fraction of lubricant that is responsible in part for high drug retention in the capsule following drug inhalation by the patient, (2) empty, closed capsules for the purpose of removing the lubricant oil without opening the capsules, (3) filled capsules for the purpose of extracting either the lubricant oil (if the capsules were not previously extracted with a SCF prior to filling with the powder blend), solvent used in the drug formulation, or trace level impurities from the carrier or drug particles, (4) impurities from drug or carrier particles not yet placed into capsules, (5) capsules, carrier or drug particles to achieve a desired moisture content level immediately prior to product packaging, or (6) any combination of such actions. In all applications of this invention, $CO_2$ or any other appropriate SCF is brought into contact with the material to be treated to effect the extraction of either lubricant, moisture or impurities from capsules, carrier particles or drug particles. This invention can find use in all areas where capsules are used for medicinal purposes, including DPI and orally administered capsules, irrespective of the type of drug involved.

Studies of the extractability of raw lubricant material as well as lubricant from hard gelatin capsules were conducted. Results from extraction of raw lubricant material were used to ascertain the conditions under which lubricant will be quantitatively extracted from open capsules. Capsules were extracted at the experimental scale in either their open, closed or locked state. Capsules in their closed state were also extracted at large scale to investigate process scalability to larger quantities of capsules. The results of large scale extraction are presented in a separate section. The effect of drug and carrier on retention and FPM are also presented in a separate section.

Lubricant extract and residue were analyzed by HPLC. Capsule brittleness before and after extraction was determined, and SEM was used to analyze changes in the surface of capsules brought about by the SFE process. Drug retention and FPM yielded by both SFE-treated capsules and unextracted capsules (i.e. control capsules as supplied by the manufacturer) were assessed using an Andersen cascade impactor (C.I.).

EQUIPMENT AND PROCEDURES

Experimental extraction experiments were conducted using an in-house built SFE unit. Extraction procedures and analytical methods were all developed in-house. Large scale extractions demonstrating the feasibility of process scaleup were conducted by a corporation specializing in SFE. The following section describes the experimental SFE unit. The larger scale SFE unit operates under similar principles.

EXPERIMENTAL SFE EQUIPMENT

As set forth above, the present invention involves the use of SCFs. FIG. 1 shows a flow diagram of an experimental unit, that can be used to conduct SFE of capsules or drug formulations, the subject of the present invention.

The SFE unit, along with a process control and monitoring system, were designed and assembled from parts and equipment from various suppliers. However, an SFE unit may also be purchased from ISCO Inc. (Lincoln, Nebr.) and Applied Separations (Allentown, Pa.). The unit consists of three sections: the feed section (1–15), the extraction section which also encompasses process parameter monitoring and control (16–22), and the flow measurement and extract recovery section (23–25). A computer (26) equipped with a data acquisition and control system along with a micrometering valve control system is used to monitor and control pressure in the extraction vessel (19), and monitor temperature in the extraction vessel and flow rate through the mass flow meter (25). A separate unit attached to the water bath (20) is used to monitor and control its temperature. The SFE unit can be, for instance, used to extract a drug and/or carrier, raw lubricant, lubricant from open capsules, empty closed capsules or filled locked capsules. The fundamental procedures are similar for such uses.

EXPERIMENTAL SFE OF DRUG POWDER, RAW LUBRICANT OR OPEN CAPSULES

The extraction procedure for either drug powder, raw lubricant or open capsules is generally as follows. Referring to FIG. 1, a known amount of material to be extracted is loaded into a 350 mL high pressure vessel (19) (High Pressure Equipment (HPE), Erie, Pa., model #GC-9). The vessel (19) is then tightly closed and placed in an isothermal water bath (20) (Polyscience Niles, Ill.)). The vessel (19) is then allowed to thermally to equilibrate with the water bath (20) for a few minutes.

Carbon dioxide with varying levels of purity may be used for extraction, including food grade $CO_2$ (minimum purity 99.2%), the SCF chromatography grade $CO_2$ used in this laboratory study (minimum purity of 99.9995%), or SFE grade $CO_2$ which can contain impurities at a level as low as 100 parts per trillion. $CO_2$ in a cylinder (1) equipped with an eductor or syphon tube (2) and a pressure gauge (3), is thus allowed into the vessel until pressure reaches about 900 psig. $CO_2$ is then pumped at a constant rate using a positive displacement, high pressure pump (4) (Thermo Separation Products, Riviera Beach, Fla., Model #396-89). until pressure in the extraction vessel reaches the desired level. The head of pump (4) is cooled, for example, with an ethylene glycol solution at −10° C. pumped with a circulating water bath. Alternatively, gaseous $CO_2$ may be pumped through the unit using a compressor.

Figure 2:
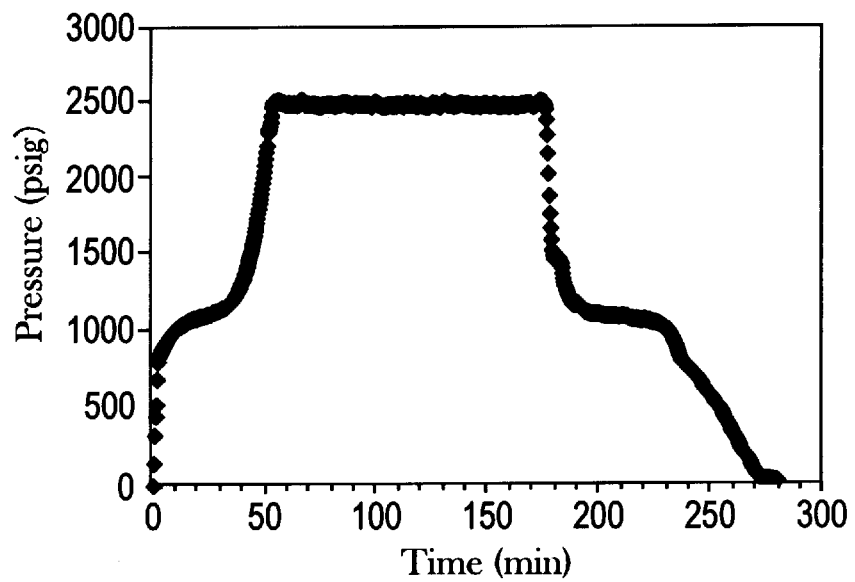

$CO_2$ is thus pumped from cylinder (1) through a check valve (5), (Norwalk Valve & Fitting (NV&F), Shelton, Conn.) to avoid backflow of $CO_2$ into the pump (4), a rupture disc (16)(HPE) for safe evacuation of the content of the unit into the hood in the event that over-pressure develops in the unit, one or more pressure relief valves (7), (NV&F) to control the rate at which $CO_2$ is first introduced into the vessel (19) a shut-off valve (8) (NV&F), and a ⅛" O.D. stainless steel heat exchanger line (15) prior to entering the high pressure vessel (19). The effluent shutoff valve (21) is initially kept closed until pressure in the vessel (19) reaches the desired extraction pressure. When the desired pressure is reached, the effluent shutoff valve (21) is opened and flow through the micrometering valve (22), (Autoclave Engineers (AE) Model 30VRMM) is established. Pressure control is accomplished using a digital control system, a pressure transducer (17) (Omega, Stamford, Conn., Model PX605) and a stepper motor (Model# M061-LE08) coupled with a 50/1 gear ratio torque enhancer (both from Minarik CO, Bristol, Conn.). Pressure is normally controlled to within ±20 psi using a proportional-integral-derivative control scheme. A 5,000 psig pressure gauge (16) (AE), and a 1/16" thermocouple (18), (Omega) inserted in a thermowell through the cap of the high pressure vessel (19) are used to monitor the temperature and pressure in the vessel (19) respectively. $CO_2$ loaded with extract expands through the micrometering valve (22) into a cold finger trap (24) for the extract, and nearly pure $CO_2$ then flows through an electronic mass flowmeter (25) (Omega, Model FMA 1700) on to the atmosphere. FIG. 2 depicts a typical temporal change in pressure in an SFE experiment. A dynamic extraction period refers to the period where pressure is controlled at 2,500 psig while continuous flow of $CO_2$ through the micrometering valve is maintained.

A 10 psig pressure relief valve (23) is used to vent effluent $CO_2$ and thereby protect the mass flowmeter (25) in the event that overpressure develops in the effluent line. At the end of the dynamic extraction period, pressure is slowly brought down to atmospheric level and the unextracted, residual material is then removed from the vessel, weighed and readied for analysis. The extract trapped in the effluent lines is flushed out with a 60% ethanol/ 40% THF solution, combined with the extract recovered in the cold finger trap (24), and then stored in amber bottles in a freezer until ready for HPLC analysis. The extracted capsules are stored in small aluminum pouches and sealed until ready for analysis for brittleness, powder retention and fine particle mass. Weight loss is determined immediately following their discharge from the vessel.

SFE OF CLOSED CAPSULES

The object of the extraction is to efficiently remove lubricant material dissolved in the $CO_2$ present in the capsules. Because of mass transfer resistance between the inside of a closed capsule and the bulk $CO_2$ phase, extraction of closed capsules by conventional SFE, i.e at constant pressure as with the open capsules, does not yield complete removal of extractable lubricant from the capsules within a reasonably short extraction period. Our calculations indicate that about 20% of the lubricant in the capsule $CO_2$ phase content is transferred to the bulk phase within a period of 2 hours. About 55% of a capsule $CO_2$ phase lubricant content would be purged out of the capsule in 5 hours of dynamic extraction.

Figure 3:
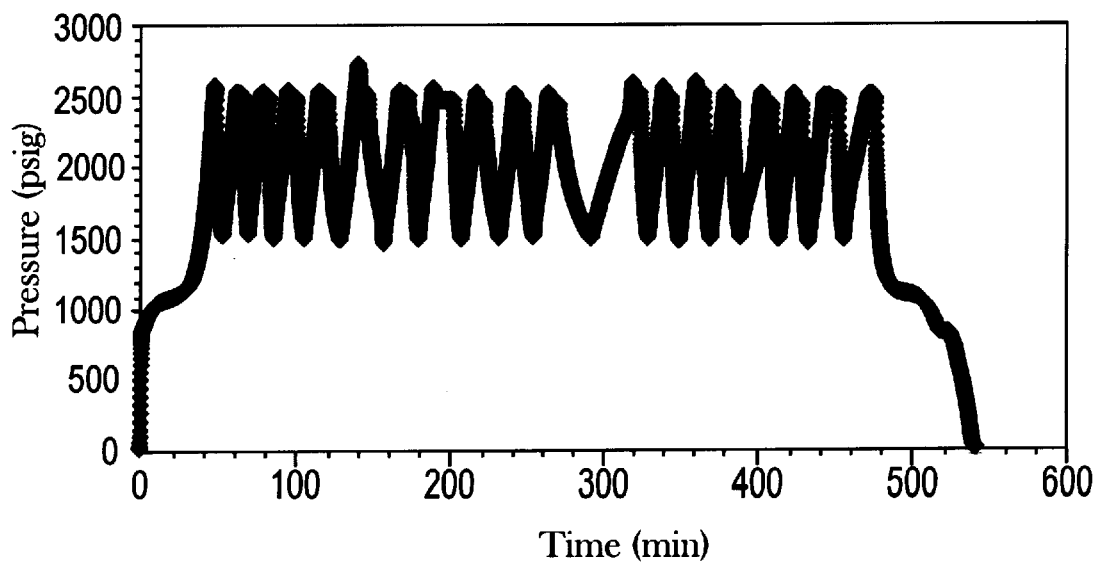

While several techniques may be used to improve lubricant extraction from closed capsules, including an increase in extraction time, pressure, temperature or $CO_2$ flow rate and fluidization of the capsule bed with $CO_2$, a pressure swing procedure whereby the content of the capsules is partially evacuated every time pressure is reduced appears to be efficient at overcoming the mass transfer barrier. A pressure swing procedure whereby the content of the capsules is partially evacuated every time pressure is reduced was thus developed to improve the extraction efficiency. The extraction procedure for closed capsules thus consists of allowing relatively large pressure swings to take place during the extraction period. This pressure-swing extraction is accomplished by bringing the vessel to a high level (for example 2,500 psig), allowing batch extraction within the capsules for 5 minutes, and then slowly reducing pressure to a lower level (1,500 psig). This latter pressure level imparts a density to $CO_2$ that is nearly 10% lower than that at 2,500 psig, but is still high enough that the extracted material will stay dissolved in the capsule $CO_2$ phase. A reduction in density by 10% implies that 10% of the lubricant in the capsule $CO_2$ phase is purged out within each pressure swing cycle. Pressure is then built up to 2,500 psig and the operation is repeated about 20 times. At the end of the 20 pressure swing cycles, the concentration of lubricant material in the capsule $CO_2$ phase is low (<7% the initial concentration), and a final reduction in pressure to atmospheric level ensures that all extractable lubricant is removed from the capsules with essentially no lubricant material re-precipitating inside the capsules. This procedure enhances mixing in the capsule $CO_2$ phase during pressure buildup, and thereby increases lubricant mass transfer rates from the capsule surface to the capsule $CO_2$ phase, as well as forcing extracted material out of the capsule into the bulk $CO_2$ phase. Under these conditions, our calculations indicate that nearly 100% of all extractable material will be purged out of the capsules. FIG. 3 depicts the change in pressure that takes place during a typical pressure-swing SFE experiment.

It should be noted that the upper pressure level can be as high as desired but preferably less than 10,000 psig, and the lower level can be as low as desired. Depending on the concentration of lubricant in the capsules and the extraction conditions and procedure, the number of pressure swings needed to extract an appreciable fraction of the lubricant can also vary.

CAPSULE BRITTLENESS

Capsule brittleness before and after extraction was determined using an instrument designed to determine the impact energy needed to pierce a capsule. The instrument consists essentially of a pin attached to the bottom of a lever swinging from increasing heights and impinging upon the capsule. The minimum height at which the capsule is pierced by the impinging pin determines the energy needed to pierce the capsule. The higher the energy (mJ) needed to pierce the capsule, the lower the capsule brittleness.

POWDER FILLING OF CAPSULES

A powder blend of lactose and ipratropium bromide (I.B.) was prepared. Powder blend uniformity was then ascertained by HPLC analysis for drug and carrier. 5.5 mg of the I.B. powder blend consisted of 5.454 mg of lactose and 0.046 mg of I.B. The powder blend was loaded into SFE-treated and control capsules. In order to assure that the majority of the lactose will not be breathed into the lungs, the powder particle size distribution is such that most of the mass of lactose resides in particles of size larger than 5.8 $\mu$m. On the other hand, in order to assure that a large fraction of the drug can potentially reach the lungs of the patient, the particle size distribution of I.B. is such that most of its mass resides in particles smaller than 5.8 $\mu$m. Capsules extracted at the experimental scale were hand-filled with the same powder batch and compared to control capsules hand-filled with the same powder. Capsules extracted at large scale were filled with an industrial size capsule filling machine with different batches of the same powder blend, and were compared to control capsules filled with the same machine.

CASCADE IMPACTOR SETUP

Figure 4:
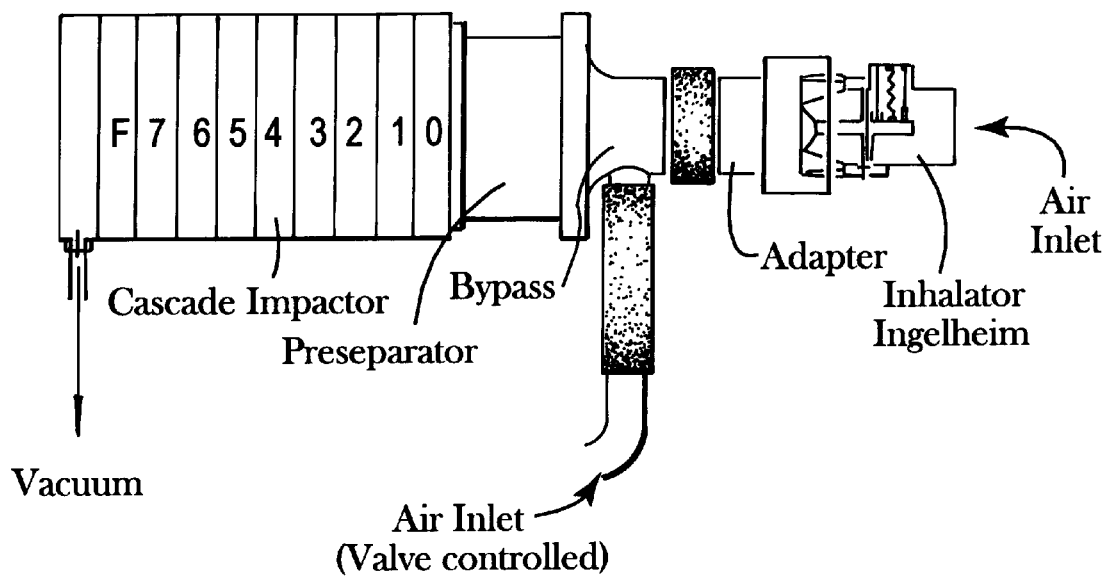
Figure 5:
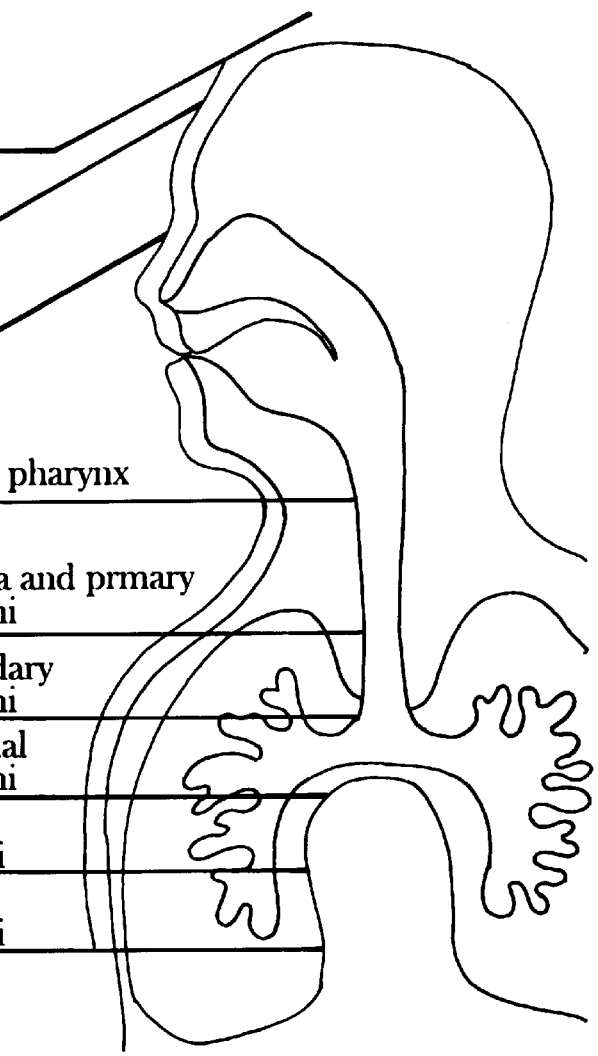

A cascade impactor (C.I.) is a standard instrument that simulates the human respiratory system. It is used to estimate the aerodynamic drug fine particle fraction that would be expected to reach the lower respiratory tract (lungs) of a patient upon drug inhalation. FIGS. 4 and 5 are schematics of the Andersen C.I. and an illustration of particle size distribution in the C.I. and its correspondence with the various segments of the human respiratory system respectively. The C.I. used in this study (Andersen 8 stage 1 ACFM non viable particle size sampler Mark II, Andersen Sampler, Inc., Atlanta, Ga., USA) is equipped with a pre-separator and an inhaler which houses the mouth piece and the filled capsule, and has been calibrated so that size ranges for each stage are as shown in FIG. 5. It consists of a series of a pre-separator stage and eight metal stages with holes of decreasing size from the top to the bottom of the stack, separated by metallic collection plates.

For operation, the capsule is first pierced with two prongs and the inhaler is closed. The piercing button is then released and a vacuum pump is used to draw the sample in the capsule through the stack of stages. The smaller the particle, the longer it remains in the air stream and the lower the stage it can reach. In order to prevent particles from bouncing off the stage plates and being entrained in the air stream, collection plates and pre-separator were coated with an adhesive material (Brij 35 in glycerol) (Broadhead, J., Edmond Rouan, S. K., and Rhodes, C. T. "Dry Powder Inhalers: Evaluation of Testing Methodology and Effect of Inhaler Design," Pharmaceutica Acta Helvetiae, 70, 1995, pp.125–131). The plates were cleaned and recoated following each run. The pre-separator was recoated once every six runs.

The C.I. is equipped with a control system which allows air to be drawn through the inhaler for a defined duration. Air flow rate and sampling time were set to 28.3 L/min. and 15 seconds respectively. Under these conditions, pressure loss due to flow resistance was 31 cm of water at a flow rate of 2.35 m$^3$/h and an air pressure of 1000 hPa. A by-pass tube is used to ascertain that pressure losses are within defined tolerances prior to conducting the test with the pierced capsule in the mouthpiece.

The I.B. lactose drug powder blend's (previously described) retention in capsules and fine particle mass (FPM, i.e. mass of particles with size <5.8 $\mu$m) in stages 2–7 of the C.I., which approximates the amount of drug delivered into the lungs of a patient, were determined. Particles collected in stages 0–1 are larger than 5.8 $\mu$m, and do not reach the bronchiolar or alveolar regions of the lungs. Particles collected from plates 2–7, which represent the respirable fraction (size <5.8 $\mu$m), were extracted together with 20 mL of 0.01N HCl. The solution was then filtered through a 0.45 $\mu$m Gelman PTFE filter. HPLC analysis was then used to determine the amount of material in plates 2–7, i.e. the FPM.

Powder retention in the capsules was determined by first opening the capsule, transferring the body and cap along with the residual powder into a 20 mL screw cap scintillation vial, adding 10 mL of 0.01N HCl, sonicating in an ice bath for 1 minute, filtering the solution through a 0.45 $\mu$m Gelman PTFE filter, and then analyzing by HPLC for I.B. and lactose. For each capsule lot, determination of retention and FPM in either extracted or control capsule lots was repeated at least 6 times. Retention and FPM for capsules extracted at the experimental scale was conducted for individual capsules. For capsules extracted at large scale, drug and carrier retention was determined for individual capsules, and FPM was determined for each stage of the impactor using the combined deposits of 10 capsules on the impactor plates. This was done to overcome limitations in detection sensitivity of the HPLC methodology.

HPLC ANALYSIS OF LUBRICANT OIL

The free linoleic acid component of lecithin is found to be prominent in the HPLC chromatogram of the type of lubricant used to manufacture the capsules used in this study. Linoleic acid was therefore selected as a reference component to evaluate the amount of lubricant in inhalation capsules. To determine the amount of linoleic acid in the raw lubricant, pure linoleic acid was injected at five different levels (4–12 $\mu$g) into the HPLC system, and a calibration curve for the peak area vs amount of linoleic acid injected was obtained. The analysis was conducted using a 4.6×250 mm, 5 $\mu$m Zorbax SB-Phenyl column and a 70/30 (v/v) acetonitrile/0.1% phosphoric acid mobile phase at 1.0 mL/min. Column temperature was set to 35° C., injection volume was 25 $\mu$l, UV detector wavelength was 210 nm, and run time was 45 min.

The amount of lubricant in capsules was determined as follows: First, 100 gelatin capsules were opened and mixed with approximately 80 mL of ethanol/tetrahydrofuran (60:40, v/v) and then sonicated in a water bath for about 5 minutes. The extract solution was then carefully transferred into a 250 mL Pyrex bottle. The shells were extracted twice with approximately 40 mL of mixed solvent, and extract solutions were then combined into the Pyrex bottle. The extract was then evaporated to dryness under a current of N$_2$. The residue was then dissolved in 5 mL of mixed solvent solution. The solution was filtered through an Acrodisc CR PTFE filter, and the filtrate was analyzed by HPLC. The amount of lubricant on the inner wall of capsules was evaluated based on the amount of linoleic acid obtained from the capsule extraction. The amount of linoleic acid is converted to the amount of lubricant based on the determined percentage of linoleic acid in the specific lubricant under study.

HPLC ANALYSIS OF DRUG AND CARRIER

Analysis for I.B. was conducted using a 4.6×150 mm Zorbax SB-C18 reverse phase column and a mobile phase of 0.008M 1-pentane sulfonic acid sodium salt/acetonitrile 82:18 (v/v) at a flow rate of 1.5 mL/min. Column temperature was 35° C., injection volume was 100 $\mu$l, UV detection wavelength was 210 nm, and run time was at least 10 minutes.

Analysis for lactose was conducted using a 7.8×300 mm Bio-Rad Aminex HPX-87H ion exclusion column and a mobile phase of 0.012 N sulfuric acid at 1.0 mL/min. Column temperature was 40° C., injection volume was 100 $\mu$l, detection was accomplished by refractive index, and run time was at least 15 minutes.

SCANNING ELECTRON MICROSCOPE (SEM) MICROGRAPHS OF CAPSULES

A scanning electron microscope (SEM, Hitachi S-4000) was used to examine changes in capsule internal surface brought about by the SFE process. Capsules were cut using a heated wire then adhered to an aluminum stub using a double sticky silver tape. The internal surface was then sputter-coated with a thin layer of platinum.

SFE OF RAW LUBRICANT MATERIAL

Laboratory studies involving the extraction of raw lubricant material used by manufacturer A in capsule manufacturing were conducted. These studies were used to determine conditions under which efficient extraction of lubricant material from capsules can be achieved.

In this study, a known amount of lubricant oil is first poured into a pre-weighed small glass beaker. The beaker and oil are then weighed together and charged into the extraction vessel. In all experiments, the water bath temperature was maintained at 35° C., and the $CO_2$ pump flow rate was roughly 1.6 SLM. At this flow rate, pressure reaches 2,500 psig after 47±2 minutes, and a subsequent 2-hour dynamic extraction at 2,500 psig would achieve the exchange of about 1 volume of the 350 mL vessel. The 35° C. temperature was selected for all runs as it is slightly higher that the critical temperature of $CO_2$ while being low enough that $CO_2$ density will be relatively high at reasonable pressures and no thermal degradation of lubricant or gelatin material will take place. The amount of lubricant used in all runs was 0.37±0.01 g, except for the run at 2,500 psig, 2 hours dynamic extraction where 0.33 g of lubricant oil was used. After extraction, the yield is calculated from the relative difference in the mass of oil prior to extraction to the mass of residual oil left in the glass beaker.

Figure 6:
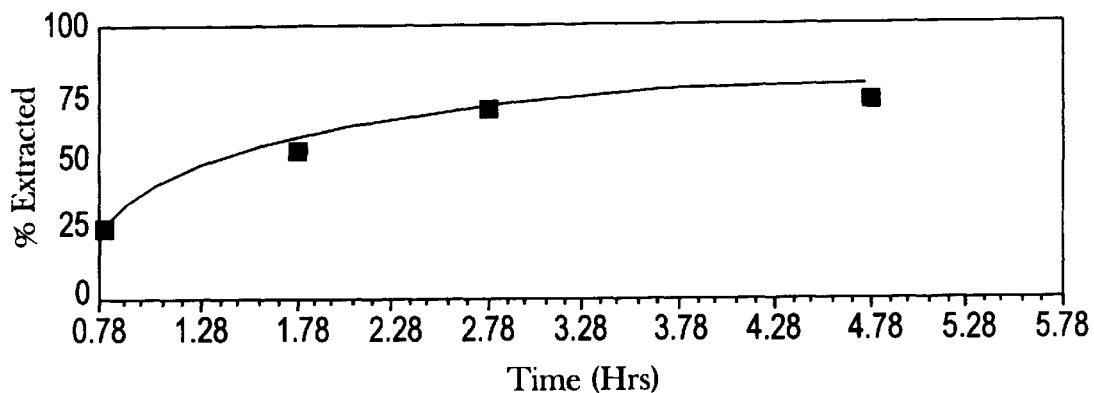
Figure 7:
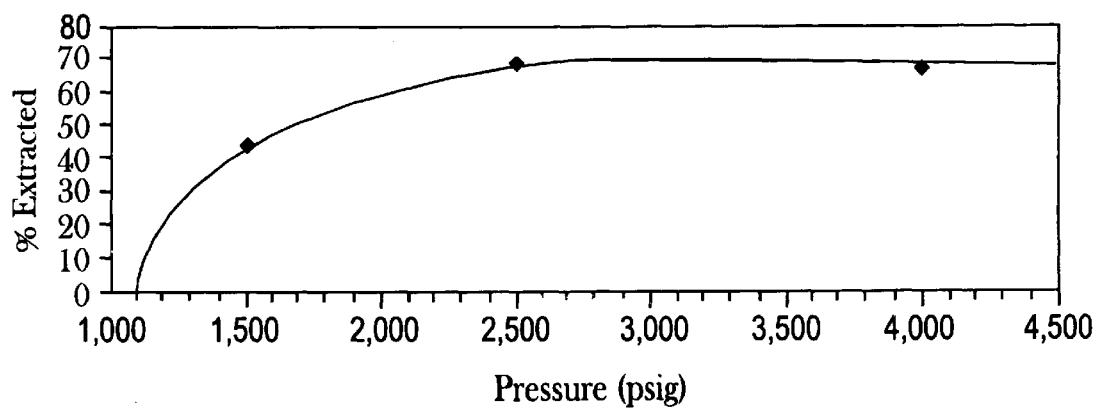

FIGS. 6 and 7 illustrate the results of extraction of the lubricant with $CO_2$ at different conditions of pressure and dynamic extraction time. FIGS. 6 and 7 indicate that both time as well as pressure affect extraction yield. FIG. 6 shows that extraction yield increases with dynamic extraction time; however, no appreciable gain in extraction yield beyond two hours of dynamic extraction at 2,500 psig is achieved. A maximum of 73.7% of the lubricant is thus extractable with $CO_2$ at 2,500 psig and 35° C. FIG. 7 shows that an increase in pressure from 2,500 psig to 4,000 psig does not yield a sensible increase in yield.

Appreciable lubricant precipitation during pressure letdown was observed only for the run where no dynamic extraction period was allowed, i.e. for the run where the vessel $CO_2$ phase was slowly purged as soon as pressure reached 2,500 psig. FIG. 6 indicates that 25.6% of the lubricant material, i.e. 94 mg of lubricant material consisting mostly of the lighter fraction of the lubricant, was dissolved in the $CO_2$ phase when pressure first reached 2,500 psig. A maximum lubricant concentration of 0.26 mg/mL was thus achieved, a value that is higher than the maximum possible concentration of lubricant in a capsule $CO_2$ phase (0.13 mg/mL based on a capsule content of 40 $\mu$g and a capsule volume of 0.3 mL). This means that during extraction of capsules, in the absence of mass transfer limitations particular to the capsules, most of the more soluble fraction of the lubricant will be in the capsule $CO_2$ phase as soon as pressure reaches 2,500 psig.

Oil residues from experiments at 2,500 psig and dynamic extraction time >2 hours appeared as solid-like glassy material, while residues from other experiments appeared still liquid-like, though more viscous than neat lubricant oil. Hence, 2 hours of dynamic extraction at 2,500 psig should lead to essentially optimal recovery of extractable lubricant from capsules and to the extraction of nearly all of the liquid fraction of the lubricant which is hypothesized to be responsible for most of the drug retention in capsules.

The effect of adding an organic solvent to $CO_2$ on its ability to extract more lubricant was also investigated. In this study, 30.8 mL of ethanol were first poured into the vessel followed by loading of 0.38 g of lubricant oil in a glass beaker. This method of adding a modifier, as opposed to pumping the modifier separately and mixing it with $CO_2$ prior to entering the extraction vessel, is simpler and can be used to ensure that the $CO_2$/ethanol phase contacting the lubricant is unsaturated or nearly-saturated and supercritical. The extraction was conducted at 2,500 psig for 8 hours to ascertain that all the ethanol is completely purged from the vessel by the end of the dynamic extraction period. HPLC analysis of the extract recovered in the cold trap indicates that the presence of ethanol increases the recovery of lubricant oil compounds such as linoleic acid, but overall recovery was still similar to that obtained with pure $CO_2$ at 2,500 psig and 4 hours of extraction time (73.7%). This study thus indicates that operation at 2,500 psig for 2 hours should lead to nearly maximum recovery of extractable oil from capsules and to the extraction of nearly all of the liquid fraction of the lubricant oil.

Capsule extraction was conducted at both laboratory (experimental scale, 112 capsules), pilot (9,000 capsules) scale, as well as large scale (250,000 capsules). The following section presents results of extraction of capsules at a scale up to 9,000 capsules.

LABORATORY EXTRACTION OF LUBRICANT MATERIAL FROM CAPSULES:

EFFECT ON CAPSULE WEIGHT LOSS, BRITTLENESS, INTERNAL SURFACE AND DRUG AND CARRIER RETENTION AND FPM

Following extraction, capsule weight loss, brittleness and drug and carrier retention and FPM were determined. The results were then compared to the respective properties of control capsules.

PROCESSING CONSIDERATIONS

The above studies of the extraction of raw lubricant and analyses indicate that preferably, where this specific lubricant and the above extraction temperature and $CO_2$ flow rate are used, in order to achieve nearly complete removal of the soluble fraction of the lubricant, open capsules should be extracted at a pressure ±2,500 psig and a dynamic extraction time ±2 hours, and closed capsules should be extracted using the pressure swing method. Indeed, our studies indicate that extraction of open capsules at 2,500 psig and a dynamic extraction time of 1 hour yields capsules with similar overall capsule weight loss (i.e. loss of moisture+lubricant+possible other impurities) and lower retention than control (i.e. unextracted) capsules, but higher retention than capsules extracted for 2 hours at the same pressure. This indicates that 1 hour of dynamic extraction time is insufficient to effect complete removal of extractable lubricant and that 2 hours of extraction are sufficient to achieve optimum enhancement in capsule performance. Similarly, extraction of closed capsules at a constant pressure of 2,500 psig and a dynamic extraction time of 2 hours also yielded capsules with similar overall weight loss and lower retention than control capsules but much higher drug and carrier retention than capsules extracted by the pressure swing method. We conclude that extraction of moisture and possibly some small amounts of other extractable material other than lubricant does not contribute in any appreciable way to a reduction in drug and carrier retention, and that transfer of the content of the capsule $CO_2$ phase, i.e. $CO_2$+lubricant, to the bulk $CO_2$ phase (nearly pure $CO_2$) is necessary to effect a large reduction in drug retention. The results of studies of the effect of extracting capsules at nearly optimum conditions, i.e. at a pressure of 2,500 psig and a dynamic extraction time of 2 hours for open capsules and using the pressure swing method for closed capsules, on drug and carrier retention and FPM are provided here.

Table 1 depicts the conditions of extraction of capsules from two different manufacturers. Single digit capsule lot numbers (1–4) refer to control lots. Four lots of hard, pigmented gelatin capsules from different manufacturers and having different powder retention characteristics were used in this study. Capsule lot numbers followed by E indicate extracted capsules under conditions specified in Table 1. Capsule lots 1–3 are regular, i.e. commercially available, gelatin capsules from manufacturer A. Capsule lot 4 consists of regular gelatin capsules from manufacturer B. Except for capsule lot 1 which was extracted at pilot scale (~9,000 capsules), all other lots were extracted at laboratory scale. All capsules used in this C.I. study were hand-filled with the same batch of I.B./lactose powder blend (previously described).

TABLE 1

Reference Conditions for the Extraction of Open Capsules at (2,500, 35° C., 2 hours of Dynamic SFE) and Closed capsules Under Pressure Swing Conditions (2,500–1,500 psig, 35° C. psig)

| Control Capsule Lot # | SFE-Treated Capsule Lot # | Method of Extraction | State of Capsules | Mass of Untreated Capsules (g) | Mass of SFE-Treated Capsules (g) | Mass Loss (g) | % Mass Loss |
|---|---|---|---|---|---|---|---|
| 1 | 1E | Pressure Swing | Closed | — | — | — | — |
| 2 | 2E1 | Constant Pressure | Open | 5.31 | 5.18 | 0.13 | 2.40 |
| 2 | 2E2 | Pressure Swing | Closed | 5.24 | 5.11 | 0.12 | 2.30 |
| 3 | 3E | Constant Pressure | Open | 5.24 | 5.16 | 0.08 | 1.50 |
| 4 | 4E | Pressure Swing | Closed | 5.59 | 5.58 | 0.01 | 0.20 |

— Value Not Measured

Most capsules feature distinct small grooves and protuberances designed to avoid build up of air pressure and possible damage to the capsules when locked. These grooves are believed to facilitate the transfer of supercritical $CO_2$ in and out of the capsules with no physical damage; however, closed capsules withstand best the SFE process when pressure buildup is conducted at a relatively slow rate. All capsules can be extracted in their closed state with no damage if initial pressure buildup is relatively slow. For this study, the color and overall appearance of SFE-treated capsules were similar to those of control capsules. Capsules from lot 4 are least affected by the SFE process, irrespective of operating conditions and whether they are extracted in their open, closed or even locked state. Open capsules are not affected by the SFE process.

Capsule Weight Loss Due to SFE

As shown in Table 1, a weight reduction of the capsules was noted following each extraction. A wide range in weight loss is noted (0.2–2.4%). This change in weight is, however, only approximate as capsules tend to recover some of their weight loss following exposure to the atmosphere upon discharge from the vessel. The prevailing relative humidity (RH) of the atmosphere prior to extraction also affects moisture content of the capsules and hence their relative weight loss due to SFE.

Weight loss of capsules from manufacturer A varied in a relatively tight range (1.5–2.4%) even though experiments were conducted over a period of 5 months where potentially large changes in atmospheric relative humidity (RH) occurred. Weight loss is lowest for lot 4. The validity of this latter result was verified in a larger scale SFE of lot 4 (30,000 capsules) where weight loss amounted to 0.3%. Hence, lot 4 appears to contain the smallest amount of extractable material (moisture+lubricant+possibly other extractable material). Because of the small total amount of lubricant in the capsules (<4.5 mg), it is obvious that this weight loss (80–130 mg) cannot be accounted for by lubricant extraction only.

We have determined that moisture adsorption and desorption isotherms of all capsules are nearly identical, i.e. equal to that of the gelatin material; therefore, most of the observed differences in weight loss should be accounted for by differences in the prevailing relative humidity prior to extraction and to differences in the loss of extractable material other than moisture. In order to eliminate the effect of the prevailing atmospheric RH and determine the fraction of extractable material attributable to material other than the lubricant and moisture, capsules from control lots 2 and 4 were conditioned in a 53.3% RH environment over a saturated solution of Mg(NO3)$_2$ for 48 hours prior to their extraction. The capsules were then weighed and extracted in their open state for 2 hours at 2,500 psig. The extracted capsules were then conditioned for 48 hours over the same solution, and then weighed again to determine the fractional weight loss that is not due to moisture loss. Under these conditions, weight loss for lots 2 and 4 amounted to 0.52% and 0.45% respectively, i.e 239 µg and 207 µg respectively for a capsule weight of 46 mg. Hence, similarly with our previous findings based on un-conditioned capsules, capsule lot 4 exhibits lower amounts of extractable material other than moisture and lubricant respectively.

Excluding loss of lubricant which is present at a level 40 µg/capsule or less, these losses would amount to roughly 170–200 µg/capsule. These losses, if statistically significant, are very small and may be attributed to the extraction of material such as organic impurities or small molecular weight gelatin material. The present invention can thus also be used as a method for extraction of impurities, soluble material, or mobile material such as moisture, within the capsule matrix that may otherwise come in contact or react with the powder blend. Diffusion of low molecular weight compounds through the gelatin material is one mechanism by which undesirable material may come into contact with the powder blend. The same method may be applied for extraction of impurities from capsules made out of material other than gelatin, such as plastic and cellulose.

HPLC OF CAPSULE EXTRACT AND RESIDUE

Figure 8:
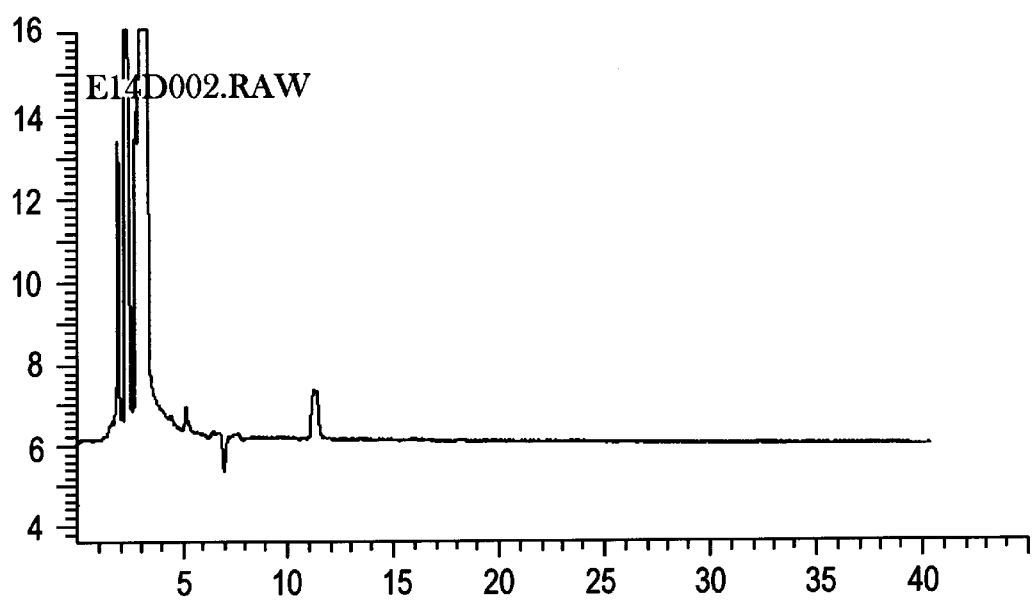
Figure 9:
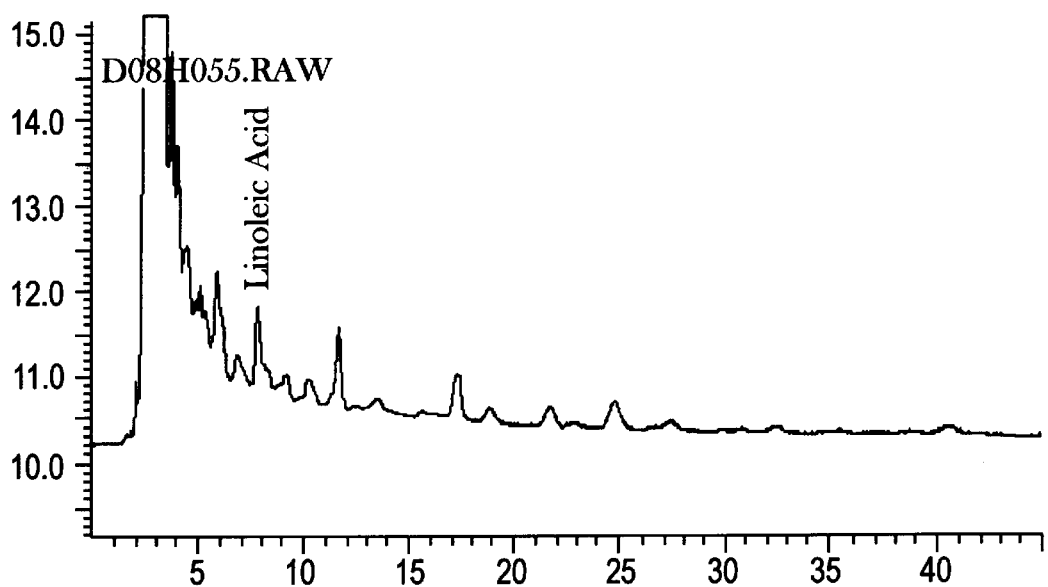
Figure 10:
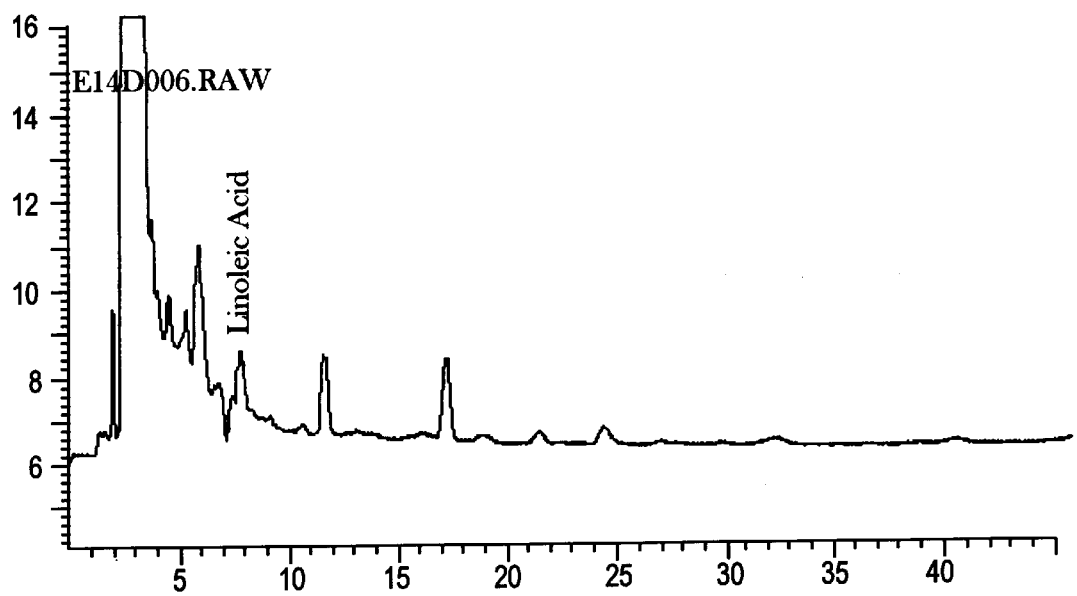

FIGS. 8 and 9 are chromatograms of the solvent elution system (Ethanol:THF) and of an extract from capsules using this solvent system. The lubricant includes a wide variety of compounds including saturated fatty acids, unsaturated fatty acids, including linoleic acid, and lecithin related materials. FIG. 10 is an example of a chromatogram of lubricant residue in capsules following their extraction by SFE. Lubricant compounds eluting close to the solvent peaks are in large concentration in the untreated capsules but are not detected in the residue. Several other compounds in the untreated capsules that eluted in the retention time window of 4–14 minutes are either in very low concentrations or no longer observed in the SFE-treated capsules. These compounds were thus extracted. It is obvious that the size and the presence of these peaks in the residue can be greatly affected by the SFE process conditions. Even under the relatively mild SFE conditions used for these SFE extractions, it is found that up to 90% of the linoleic acid component of the lubricant in the capsules is extracted.

CAPSULE BRITTLENESS FOLLOWING SFE

Table 2 shows that capsules subjected to SFE are more brittle than untreated capsules. This level of brittleness is similar to that achieved by kinetic drying at 21° C./22% RH for the purpose of reducing the moisture content of the capsules to a level below 12.4% and thereby minimize contact between moisture and the drug powder. Excessive moisture can, for some products, lead to particle agglomeration and possible hydrolysis of drug molecules. The SFE technique can thus be alternatively used to achieve this same level of dryness of the capsules.

TABLE 2

Force (mJ) Required to Pierce Control (Untreated) and SFE-treated Open and Closed Capsules at 2,500 psig, 35° C..

| Lot # | 2 (in 53.3% RH) | 3 (in 53.3% RH) | 2E1 | 3E | 2E1 (in 53.3% RH) | 3E (in 53.3% RH) |
|---|---|---|---|---|---|---|
| Force | 38 | 42 | 28 | 32 | 44 | 48 |
|  | 36 | 36 | 21 | 32 | 44 | 44 |
|  | 38 | 34 | 21 | 24 | 48 | 48 |
|  | 46 | 38 | 24 | 21 | 48 | 44 |
|  | 40 | 44 | 28 | 21 | 44 | 48 |
|  | 36 | 46 | 17 | 28 | 44 | 48 |
|  | 40 | 40 | 21 | 28 | 48 | 36 |
|  | 46 | 42 | 32 | 21 | 44 | 48 |
|  | 38 | 38 | 21 | 28 | 44 | 48 |
|  | 40 | 38 | 32 | 28 | 48 | 48 |
| Average | 39.8 | 39.8 | 24.5 | 26.3 | 45.6 | 46.0 |

Table 2 shows that SFE-treated capsules conditioned in a 53.3% RH environment exhibit a brittleness that is slightly lower than that of conditioned control capsules but much lower than that of un-conditioned, SFE-treated capsules. This indicates that the change in capsule brittleness following SFE is reversible and caused mostly by moisture removal by $CO_2$. Indeed, the color, mechanical properties and chemical properties of extracted and conditioned capsules appear identical to those of control capsules. The slightly lower brittleness of conditioned SFE-treated capsules, coupled with the small capsule weight loss (200 µg/capsule) observed for extracted capsules, points to the possibility that extracted material was substituted with moisture upon equilibration of the SFE-treated capsules.

SEM OF CAPSULES

Figure 11:
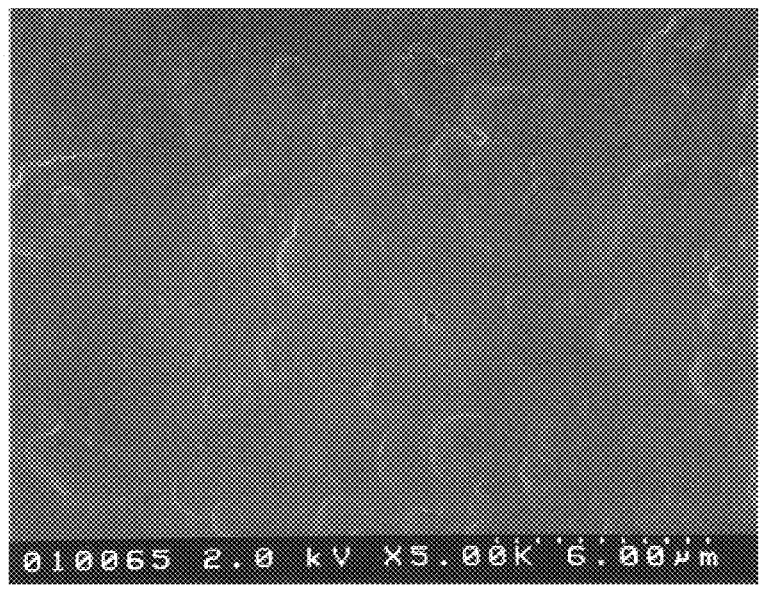
Figure 12:
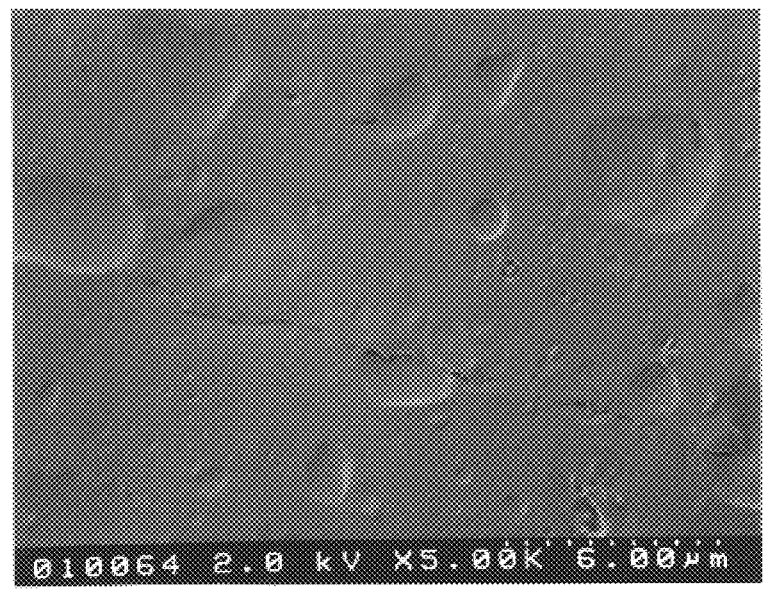

SEM micrographs of internal surfaces of control capsules show that lubricant material is distributed throughout the capsule as droplets of different contact angles with the gelatin surface. Lubricant droplets also appear to be of different sizes. On the other hand, SFE-treated capsules do not show any of the fluid, lubricant material. The surface appears to be dry, and peaks and valleys on the gelatin surface are better visualized than on control capsules because of lubricant removal. FIGS. 11 and 12 illustrate this finding.

DRUG AND CARRIER RETENTION AND FINE PARTICLE MASS (FPM)

Figure 13:
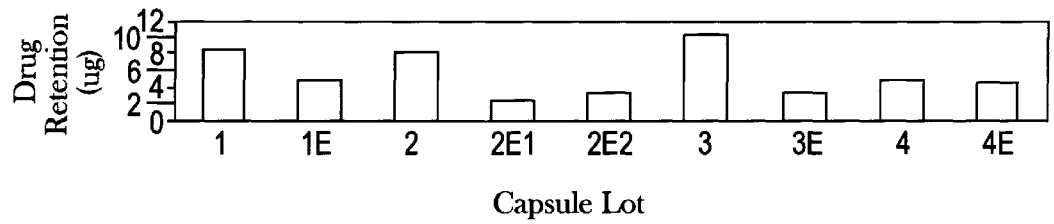
Figure 14:
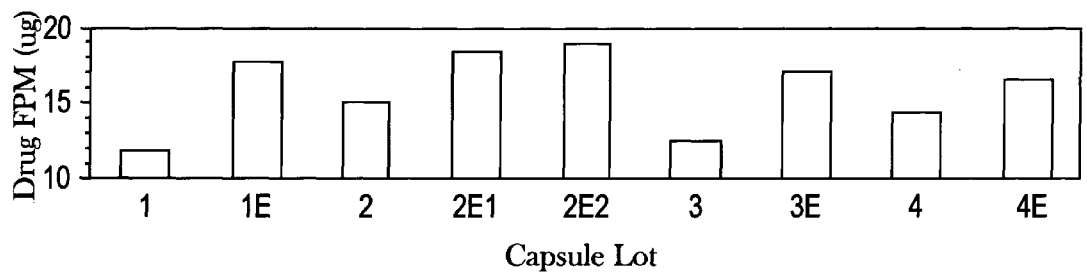
Figure 15:
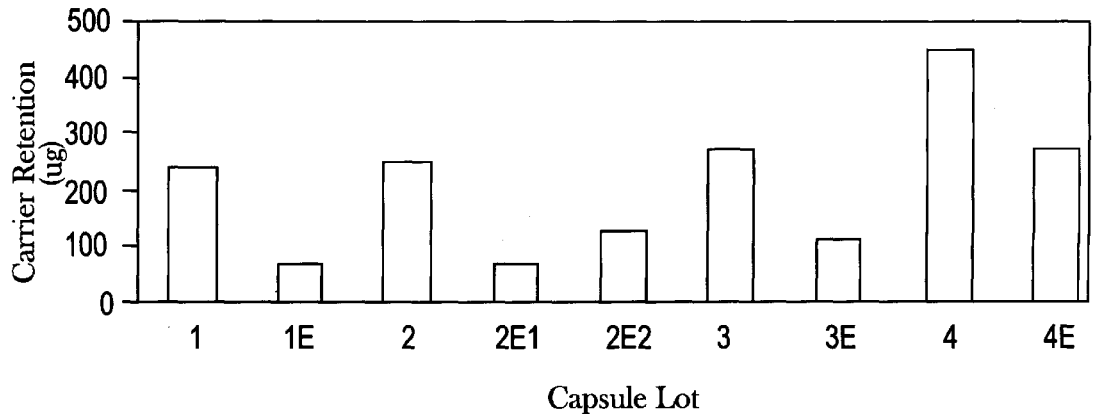

Tables 3–6 show the results of Andersen C.I. determinations of drug and carrier retention and FPM. FIGS. 13–16 are graphical illustrations of these results. Tables 3 and 5 and FIGS. 13 and 15 show that SFE-treated capsules retain less drug and carrier than the control capsules irrespective of manufacturer and whether the capsules were extracted in the open or closed state.

TABLE 3

Drug Retention (µg/Capsule) in Control Capsules and SFE-Treated Capsules

| F | 1 | 1E | 2 | 2E1 | 2E2 | 3 | 3E | 4 | 4E |
|---|---|---|---|---|---|---|---|---|---|
| 1 (n = 6) | 6.21 | 5.13 | 7.29 | 2.32 | 1.90 | 10.57 | 3.30 | 2.66 | 4.13 |
|  | 11.11 | 4.87 | 6.77 | 2.06 | 3.69 | 11.62 | 1.43 | 2.23 | 4.02 |
|  | 6.68 | 4.73 | 9.21 | 2.03 | 3.39 | 14.45 | 2.21 | 4.91 | 3.83 |
|  | 9.95 | 5.46 | 9.15 | 5.52 | 3.51 | — | 2.86 | 7.80 | 4.65 |

TABLE 3-continued

Drug Retention (µg/Capsule) in Control Capsules and SFE-Treated Capsules

| F | 1 | 1E | 2 | 2E1 | 2E2 | 3 | 3E | 4 | 4E |
|---|---|----|---|-----|-----|---|----|---|----|
|   | 8.58 | 4.44 | 8.05 | 2.44 | 2.96 | 9.90 | 3.15 | 5.95 | 4.29 |
|   | 6.08 | 5.52 | 8.27 | 2.45 | 2.50 | 14.83 | 2.17 | 5.70 | 5.13 |
| 2 |  | 4.79 | 8.15 | 1.80 | 2.80 | 10.57 | 3.65 |  |  |
| (n = 6) |  | 5.20 | 6.60 | 2.20 | 2.15 | 10.47 | 3.94 |  |  |
|   |  | 3.39 | 6.58 | 1.85 | 2.42 | 13.27 | 1.97 |  |  |
|   |  | 4.07 | 11.14 | 2.36 | 3.23 | 7.96 | 5.09 |  |  |
|   |  | 3.97 | 9.01 | 1.30 | 3.00 | 6.66 | 3.56 |  |  |
|   |  | 4.62 | 9.77 | 1.55 | 4.23 | 8.18 | 2.35 |  |  |
| 3 |  | 4.17 | 9.77 | 2.16 | 3.16 | 9.93 | 2.78 |  |  |
| (n = 6) |  | 3.58 | 8.14 | 2.59 | 2.61 | 8.53 | 2.70 |  |  |
|   |  | 6.37 | 8.75 | 3.48 | 3.58 | 8.05 | 2.92 |  |  |
|   |  | 3.18 | 5.34 | 2.16 | 4.11 | 8.77 | 5.02 |  |  |
|   |  | 4.54 | 7.61 | 2.09 | 2.86 | 9.68 | 4.18 |  |  |
|   |  | 5.09 | 7.09 | 1.30 | 4.23 | 12.38 | 3.21 |  |  |
| Average | 8.10 | 4.62 | 8.15 | 2.31 | 3.13 | 10.34 | 3.14 | 4.88 | 4.35 |
| St. Dev. | 2.1 | 0.8 | 1.4 | 0.9 | 0.7 | 2.3 | 1.0 | 2.1 | 0.5 |

TABLE 4

Fine Particle Mass (µg/Capsule) of Drug Yielded by Control Capsules and SFE-Treated Capsules

| Run # | 1 | 1E | 2 | 2E1 | 2E2 | 3 | 3E | 4 | 4E |
|-------|---|----|---|-----|-----|---|----|---|----|
| 1 | 13.87 | 15.75 | 15.84 | 16.20 | 18.19 | 11.60 | 17.15 | 15.00 | 15.30 |
| (n = 6) | 7.88 | 17.64 | 15.73 | 18.18 | 19.38 | 11.62 | 17.31 | 16.41 | 17.46 |
|   | 11.41 | 17.22 | 19.19 | 15.29 | 19.00 | 9.16 | 15.44 | 13.74 | 17.39 |
|   | 12.09 | 17.91 | 16.83 | 16.61 | 19.79 | — | 17.38 | 12.02 | 16.61 |
|   | 11.03 | 17.10 | 13.55 | 18.58 | 20.57 | 14.15 | 18.86 | 14.31 | 16.54 |
|   | 12.95 | 16.46 | 13.84 | 17.53 | 18.66 | 10.94 | 19.56 | 14.38 | 16.29 |
| 2 |  | 16.72 | 13.75 | 19.81 | 18.15 | 14.15 | 18.04 |  |  |
| (n = 6) |  | 16.77 | 14.86 | 17.88 | 19.53 | 11.47 | 17.34 |  |  |
|   |  | 16.57 | 15.89 | 19.22 | 19.97 | 10.73 | 18.16 |  |  |
|   |  | 19.08 | 13.01 | 19.83 | 18.88 | 12.71 | 19.26 |  |  |
|   |  | 18.64 | 14.13 | 20.63 | 18.90 | 12.24 | 18.09 |  |  |
|   |  | 18.16 | 13.66 | 17.72 | 18.98 | 12.29 | 19.22 |  |  |
| 3 |  | 18.79 | 13.18 | 16.46 | 17.71 | 11.54 | 12.13 |  |  |
| (n = 6) |  | 17.63 | 14.03 | 17.59 | 17.14 | 12.68 | 17.78 |  |  |
|   |  | 16.89 | 13.55 | 19.86 | 17.28 | 14.32 | 16.85 |  |  |
|   |  | 19.71 | 14.73 | 18.37 | 19.12 | 13.74 | 16.30 |  |  |
|   |  | 19.34 | 15.73 | 17.20 | 19.32 | 13.65 | 14.15 |  |  |
|   |  | 17.66 | 15.33 | 20.31 | 19.13 | 10.65 | 18.19 |  |  |
| Average | 11.54 | 17.67 | 14.82 | 18.18 | 18.87 | 12.21 | 17.17 | 14.31 | 16.61 |
| St. Dev. | 2.1 | 1.1 | 1.5 | 1.5 | 0.9 | 1.5 | 1.8 | 1.4 | 0.9 |

TABLE 5

Carrier Retention (µg/Capsule) in Control Capsules and SFE-Treated Capsules

| Run # | 1 | 1E | 2 | 2E1 | 2E2 | 3 | 3E | 4 | 4E |
|-------|---|----|---|-----|-----|---|----|---|----|
| 1 | 180.57 | 207.7 | 233.0 | 66.3 | 82.6 | 300.4 | 133.2 | 377.4 | 272.1 |
| (n = 6) | 323.14 | 174.1 | 220.9 | 130.7 | 148.8 | 288.3 | 73.6 | 264.6 | 275.5 |
|   | 230.18 | 153.9 | 233.0 | 55.1 | 118.2 | 365.5 | 101.6 | 440.7 | 213.1 |
|   | 284.09 | 215.4 | 273.5 | 76.2 | 128.1 | — | 81.5 | 611.1 | 326.1 |
|   | 237.76 | 157.7 | 245.9 | 74.8 | 127.5 | 274.1 | 99.2 | 540.8 | 262.1 |
|   | 168.23 | 222.3 | 273.7 | 85.0 | 96.4 | 330.9 | 97.1 | 470.9 | 285.5 |
| 2 |  | 174.0 | 266.8 | 75.7 | 115.7 | 264.7 | 147.1 |  |  |
| (n = 6) |  | 184.2 | 195.2 | 53.2 | 88.9 | 263.8 | 149.5 |  |  |
|   |  | 131.2 | 183.5 | 57.7 | 165.6 | 323.0 | 70.5 |  |  |
|   |  | 150.8 | 322.9 | 86.9 | 94.3 | 248.7 | 167.7 |  |  |
|   |  | 167.0 | 314.0 | 29.6 | 146.2 | 190.3 | 129.7 |  |  |
|   |  | 137.8 | 262.7 | 79.8 | 147.8 | 207.8 | 86.2 |  |  |
| 3 |  | 142.4 | 260.6 | 70.4 | 131.5 | 280.0 | 82.1 |  |  |
| (n = 6) |  | 123.4 | 220.3 | 67.1 | 106.9 | 219.1 | 136.6 |  |  |
|   |  | 244.8 | 222.4 | 134.6 | 134.4 | 223.4 | 84.3 |  |  |
|   |  | 110.9 | 182.3 | 51.5 | 134.6 | 219.9 | 151.8 |  |  |

TABLE 5-continued

Carrier Retention (µg/Capsule) in Control Capsules and SFE-Treated Capsules

| Run # | 1 | 1E | 2 | 2E1 | 2E2 | 3 | 3E | 4 | 4E |
|-------|---|----|---|-----|-----|---|----|---|----|
|   |  | 161.0 | 224.5 | 52.0 | 100.1 | 288.5 | 104.9 |  |  |
|   |  | 203.3 | 239.9 | 25.4 | 147.3 | 325.8 | 131.2 |  |  |
| Aver. | 237.33 | 170.1 | 243.1 | 70.7 | 123.0 | 271.4 | 112.7 | 450.9 | 274.4 |
| St. Dev. | 59.3 | 62.6 | 39.1 | 28.2 | 24.0 | 49.1 | 30.8 | 121.7 | 40.6 |

TABLE 6

Fine Particle Mass (µg/Capsule) of Carrier Yielded by Control Capsules and SFE-Treated Capsules

| Run # | 1 | 1E | 2 | 2E1 | 2E2 | 3 | 3E | 4 | 4E |
|-------|---|----|---|-----|-----|---|----|---|----|
| 1 | 191.3 | 276.5 | 179.2 | 236.9 | 285.6 | 162.1 | 229.0 | 328.5 | 277.6 |
| (n = 6) | 120.0 | 287.2 | 188.1 | 234.1 | 312.9 | 172.9 | 230.1 | 334.5 | 292.7 |
|   | 175.2 | 280.1 | 230.5 | 331.8 | 281.7 | 115.9 | 202.2 | 293.2 | 289.4 |
|   | 172.1 | 285.9 | 191.3 | 266.9 | 305.0 | — | 215.1 | 273.2 | 279.1 |
|   | 161.1 | 285.4 | 186.5 | 290.0 | 315.2 | 187.1 | 208.8 | 277.8 | 281.0 |
|   | 191.6 | 288.1 | 169.4 | 274.6 | 289.9 | 133.6 | 262.0 | 287.5 | 286.4 |
| 2 |  | 99.8 | 198.0 | 263.4 | 294.6 | 190.6 | 224.7 |  |  |
| (n = 6) |  | 286.6 | 214.3 | 241.9 | 315.4 | 142.9 | 216.0 |  |  |
|   |  | 289.5 | 201.8 | 457.3 | 317.3 | 130.9 | 238.1 |  |  |
|   |  | 312.4 | 211.2 | 277.2 | 305.7 | 162.7 | 225.6 |  |  |
|   |  | 308.2 | 190.2 | 286.0 | 312.7 | 156.4 | 209.9 |  |  |
|   |  | 303.5 | 191.9 | 247.3 | 293.0 | 158.3 | 234.1 |  |  |
| 3 |  | 302.2 | 154.5 | 220.2 | 290.6 | 156.0 | 140.8 |  |  |
| (n = 6) |  | 292.0 | 170.2 | 240.8 | 264.9 | 169.2 | 197.5 |  |  |
|   |  | 275.1 | 171.2 | 266.8 | 266.1 | 195.6 | 219.2 |  |  |
|   |  | 311.4 | 189.5 | 250.1 | 302.3 | 182.5 | 201.0 |  |  |
|   |  | 305.3 | 205.6 | 235.4 | 304.9 | 180.2 | 182.3 |  |  |
|   |  | 273.8 | 193.8 | 270.6 | 323.7 | 132.9 | 240.2 |  |  |
| Average | 168.6 | 292.4 | 191.0 | 271.7 | 299.0 | 160.6 | 215.4 | 299.1 | 285.0 |
| St. Dev. | 26.5 | 36.8 | 18.3 | 53.2 | 17.0 | 23.3 | 26.3 | 26.0 | 6.55 |

Among the control capsules, capsules from manufacturer B (lot 4) exhibit the highest FPM and lowest retention. The FPM of control capsules from lot 2 is close to that of lot 4, but their retention is substantially higher.

Retention in SFE-treated capsules from manufacturer A are 2–4 times smaller than retention in their corresponding control capsules. The smallest drug and lactose retention levels were achieved with capsules from lot 2. SFE-treated lot 2 also reproducibly yields drug FPM in the order of 18.5 µg (40% of total dosage). The reduction in drug retention in lot 4 capsules by SFE is smaller than for other capsules due to the fact that control lot 4 capsules already retain relatively small amounts of drug; however, unlike control capsules from lot 4 which exhibited a retention in the range of 2.2–7.8 µg, capsule retention within extracted capsules from the same lot is within 3.8–5.1 µg. Hence, SFE-treated capsules have more uniform retention properties than untreated capsules irrespective of their retention properties, and SFE can thus be used to ascertain the quality of capsules irrespective of their source.

Tables 3 and 4 show that all capsules can be treated by SFE to yield average drug retentions in the range of 2.0–5.0 µg (4–11%) and FPM in the range of 16.5–19.0 µg (36–41%), irrespective of capsule lot and capsule manufacturer. This compares to average drug retention in the range of 4.5–10.5 µg (10–23%) and average FPM in the range of 12.0–15.0 µg (26–33%) in the corresponding control capsules. The higher drug retention in control capsules than in extracted capsules proves that the SFE process attenuates greatly the drug retention ability of the capsules. As expected, lower drug retention in SFE capsules is accompanied by a commensurate increase in FPM. The overall retention and FPM for combined extracted lots 1–4 amount to 3.5±0.9 μg, and 17.7±0.9 μg respectively. Hence, standard deviations in either retention or FPM for combined extracted lots are small.

Figure 16:
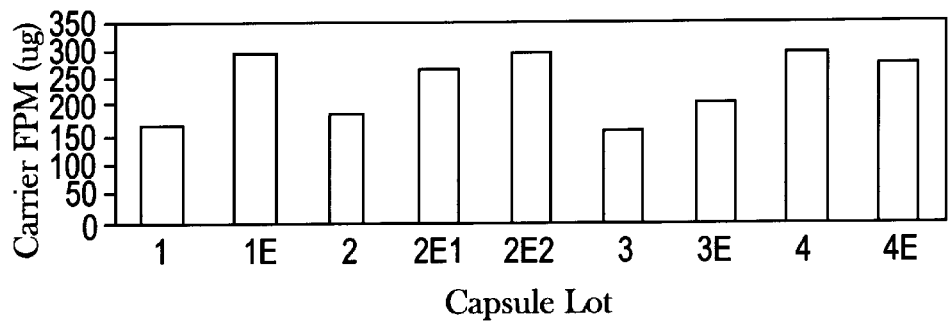

Tables 5 and 6 and FIGS. 15 and 16 show that carrier retention in extracted capsules is much lower in SFE-treated capsules than in control capsules and that carrier FPM yielded by extracted capsules is generally higher than that yielded by the control capsules. Within a capsule lot, capsule to capsule reproducibility in carrier retention is generally higher for extracted capsules. Carrier FPM is higher for extracted capsules, except in the case of lot 4 where carrier FPM was essentially not affected. Hence, both carrier retention as well as carrier FPM are positively affected by the SFE treatment.

Figure 17:
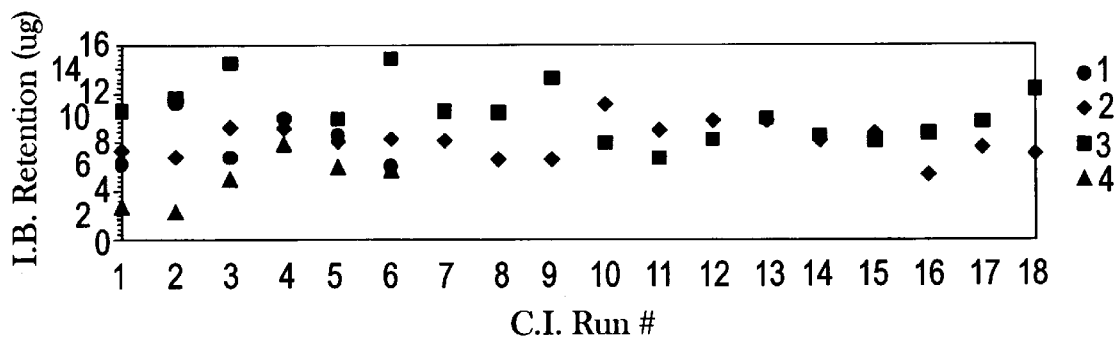
Figure 18:
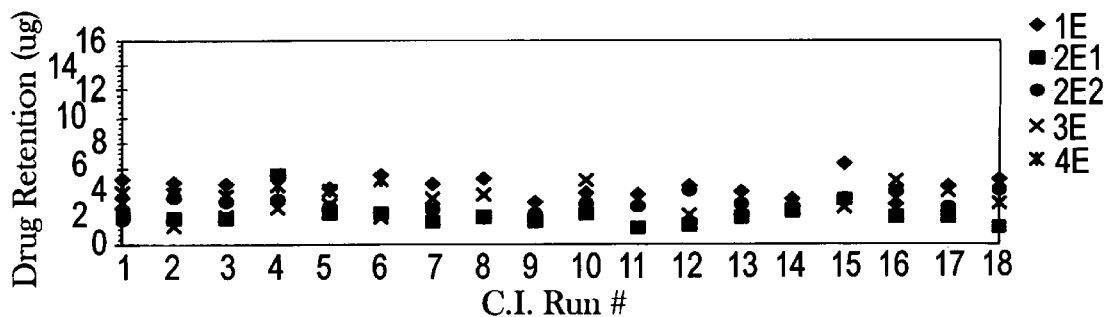
Figure 19:
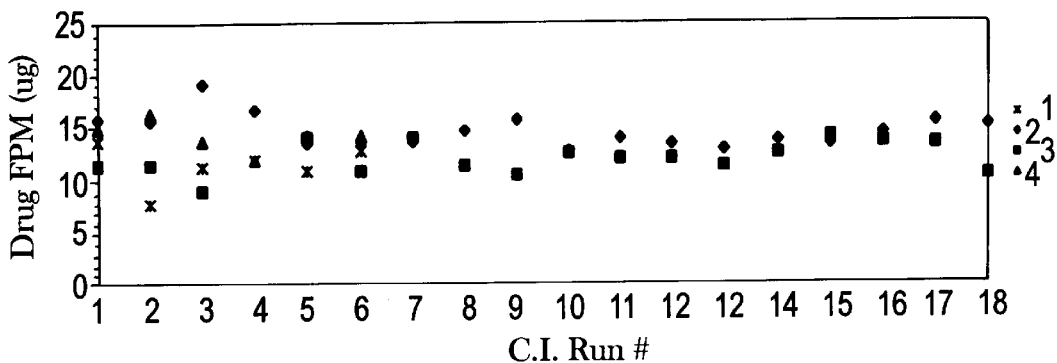
Figure 20:
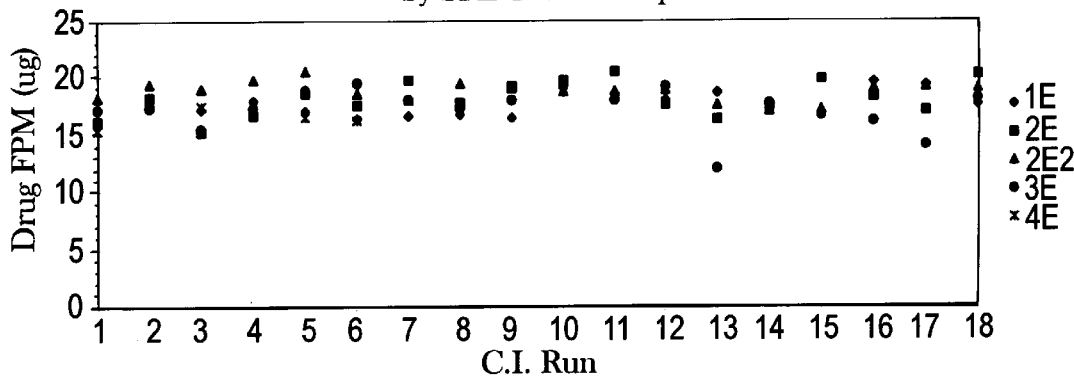

The enhancement in capsule to capsule reproducibility in drug retention and FPM by SFE of capsules is illustrated more conclusively in FIGS. 17–20 which combine all data for lots 1–4. FIGS. 17 and 18 illustrate the dramatic reduction in drug retention and the large enhancement in reproducibility in drug retention when capsules are treated by SFE. Drug retention in extracted capsules varies in the range of 1–6 μg, while retention in control capsules varies in the range of 2–15 μg. FIGS. 19 and 20 illustrate the enhancement in drug FPM and its reproducibility achieved by extracting the capsules with supercritical $CO_2$. Drug FPM yielded by extracted capsules is, in general, within ±2 μg irrespective a capsule lot. Much larger variations are observed for the control capsules. Similar enhancements in reproducibility are observed for the carrier.

The above results, including hardness measurements, chromatographic analysis of extract and residue, SEM of capsules, and drug and powder retention and FPM, all combine to demonstrate that the SFE process allows the extraction of the fraction of lubricant material responsible for high drug retention and erratic dosage with no damage to the capsules.

LARGE SCALE SFE OF CLOSED CAPSULES

This study is designed to demonstrate that the present invention can be used to treat large scale batches. Capsules of different lots, in their closed state, were thus loaded into separate cotton bags and tied separately with plastic straps. The cotton bags were then loaded successively into an 80 L cylindrical vessel and extracted by the pressure swing method (2,500–1,500 psig, 35° C.) using supercritical $CO_2$. Each cotton bag contained approximately 15,000 capsules. Nearly 315,000 capsules were extracted in 3 runs of about 105,000 capsules each. An industrial scale batch may amount to several millions of capsules.

Several lots of extracted capsules along with their corresponding control lots were then filled on an industrial filling machine with different batches of the previously described I.B./lactose powder blend. A total of 10 batches of I.B./lactose capsules were produced out of 3 regular capsule lots from manufacturer A (1, 3 and 5) and 1 regular capsule lot from manufacturer B (Lot 4). The capsules were then conditioned in a 53.3% RH environment, and then analyzed for drug retention and FPM using the Andersen C.I. Evaluation of drug and carrier retention per capsule was repeated 10 times for each lot. Each individual stage of the C.I. was analyzed for drug and powder pooled from 10 successive C.I. runs. The content of 10 capsules distributes enough powder to the pre-separator and the 8 stage plates for accurate determination of powder collection in each stage to be possible.

This study demonstrated that the process of extracting capsules by SFE for the purpose of reducing powder retention and increasing FPM is scalable to large capsule quantities. All extracted capsules retained less powder and yielded a higher drug and carrier FPM than their corresponding control capsules irrespective of lactose lot and I.B. lot. FIGS. 21 to 24 illustrate this finding for I.B. Similar results were obtained for lactose.

Figure 21:
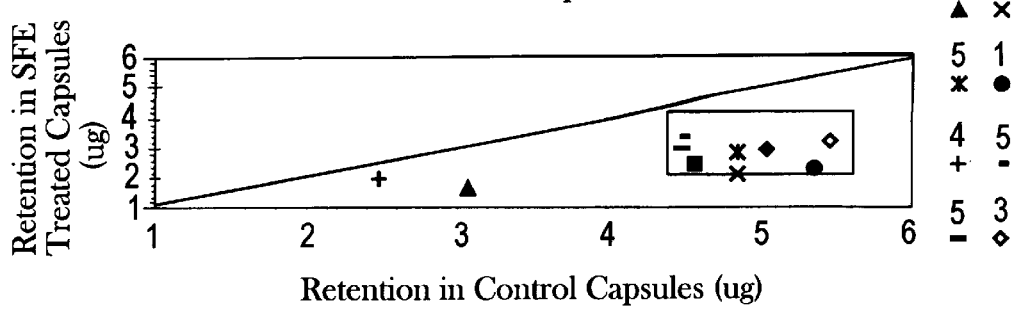

FIG. 21 indicates that SFE-treated capsules retain less drug than their corresponding control capsules irrespective of capsule lot, drug lot or carrier lot. For combined lots, drug retention in SFE-treated capsules is distributed within a narrower range than retention in control capsules (1.5–3.5 μg vs 2.5–5.5 μg). Average retention in SFE-treated capsules and control capsules amount to 2.6±0.6 μg and 4.5±1.0 μg respectively. As in the laboratory scale study, drug retention in control and SFE-treated capsules from manufacturer B are here again found to retain the least amount of drug.

FIG. 22 shows that SFE-treated capsules yield a higher drug FPM than control capsules irrespective of capsule lot, drug lot or carrier lot. FPM yielded by capsules from manufacturer B and their corresponding SFE-treated capsules are, in general, slightly higher than FPM yielded by capsules from manufacturer A. FPM yielded by extracted capsules from manufacturer A is nearly constant (16.7–19.2 μg), irrespective of capsule lot, drug lot or carrier lot. In contrast FPM in control capsules varies between 13.0–17.5 μg. Overall, combining all capsules, average FPM yielded by SFE-treated capsules and control capsules amount to 18.5±1.7 μg and 14.8±1.5 μg respectively.

FIGS. 23 and 24 illustrate the difference in capsule to capsule reproducibility of drug retention in control capsules and SFE-treated capsules respectively. Drug retention in control capsules varies between 1.0–10.5 μg. In contrast, drug retention in SFE-treated capsules varies in a much narrower range (1.0–5.6). SFE-treated capsules thus behave similarly with regard to drug retention, irrespective of capsule lot. Hence, as shown with laboratory scale studies, greater reproducibility in drug retention, and hence drug dosage, can be achieved with SFE-treated capsules than with control capsules.

EFFECT OF EXTRACTING DRUG, CARRIER AND DRUG POWDER WITH SUPERCRITICAL $CO_2$: RESULTS AND ANALYSIS

Studies of extraction of drug powder constituents were undertaken to determine whether adhesion properties of the carrier can be affected by extraction of impurities from the surface of particles using supercritical $CO_2$. This technique can potentially provide the ability to make the surfaces of carrier and drug particles uniform and reproducible, and therefore improve the reproducibility and yield in fine particle mass.

Filled and locked capsules were also extracted with supercritical $CO_2$. This allows for the alternative possibility of treating capsules by SFE after they are filled with drug powder.

SFE OF LACTOSE, DRUG AND POWDER BLEND

Lactose and I.B. were extracted separately at 2,500 psig and 35° C. for 2 dynamic extraction hours with $CO_2$. It was observed that no detectable mass loss resulted from either extraction and no change in size and overall appearance was detected on SEM micrographs of lactose, indicating that both lactose as well as I.B. are good candidates for treatment by SFE. SFE can thus extract impurities from both substances without substantially affecting the formulation. Impurities are, in general, in trace amounts, and can thus generally be dissolved in a SCFs such as $CO_2$. For protein-like impurities generally found on lactose, an increase in pressure to levels closer to 10,000 psig may be necessary to effect their extraction.

Tables 7 and 8 illustrate our findings. Drug powders formed from extracted lactose, as opposed to control lactose as provided by the manufacturer, are found to exhibit a higher FPM. No appreciable change in powder retention is brought about by the extraction of lactose. Hence, retention depends only on capsule properties and surface properties of lactose are important in determining the strength of adhesion of a drug to the carrier. lactose extraction can thus provide a means to control FPM. Conditioning of the capsules in a 53.3% R.H. appears to slightly increase FPM and reduce retention.

TABLE 7

Effect of Lactose Extraction on Drug and Carrier Retention and FPM
Lactose lot 1, and Drug Lot 2 Were Mixed to Form the Drug Powder.
Drug Powder was Filled into Capsule Lot 5.

| Conditions | Drug FPM (μg/caps) | Drug Retention (μg/caps) | Carrier FPM (μg/caps) | Carrier Retention (μg/caps) |
|---|---|---|---|---|
| uL + uC | 10.9 | 9.9 | 147.7 | 256.9 |
| uL + eC | 15.0 | 4.4 | 176.0 | 129.9 |
| uL + ecC | 16.0 | 2.8 | 178.9 | 83.7 |
| eL + uC | 13.2 | 8.7 | 175.5 | 206.2 |
| eL + eC | 16.1 | 2.9 | 182.0 | 92.5 |
| eL + ecC | 17.1 | 3.2 | 213.7 | 116.2 | u: Untreated; e: Extracted; c: Capsules Conditioned at 53.3% RH; C: Capsules; L: Lactose

TABLE 8

Effect of Powder Blend Extraction on
Drug and Carrier Retention and FPM
Lactose lot 1 or 2 and Drug Lot 1 Were Mixed to Form the
Drug Powder. Powder was filled into Capsule Lot 5.

| Condition of Lactose and Lot # | Drug FPM (μg/caps) | Drug Retention (μg/caps) | Carrier FPM (μg/caps) | Carrier Retention (μg/caps) |
|---|---|---|---|---|
| uB1 | 14.1 | 4.9 | 223.1 | 153.0 |
| eB1 | 13.0 | 4.9 | 282.0 | 127.6 |
| uB2 | 14.3 | 4.5 | 201.3 | 142.3 |
| eB2 | 14.0 | 5.2 | 194.8 | 170.7 | uB: Untreated Blend; eB: Extracted Blend.

Extraction of drug powder, i.e. mixed drug and carrier, is observed not to have any effect on either drug FPM or retention. The lack of effect on FPM indicates that the adhesion properties of the drug and carrier were not changed by the extraction process. Given our findings that lactose surface is affected by the SFE process, and that powder blends with extracted lactose have a different FPM than powder blends with control lactose, we conclude that the extraction of the blend does not affect the surface of adhesion between the drug and carrier. Hence, the adhesion area between the drug and the drug or carrier is not affected by the extraction process. This, in turn, implies that either the area of adhesion is not accessible to $CO_2$ or that interactive forces of adhesion between the drug and drug or carrier are stronger than the solubilizing power of $CO_2$ for the surface components of the carrier.

SFE OF FILLED AND LOCKED CAPSULES 4 lots of untreated capsules from manufacturer A (lots 1,5, and 6) and B (lot 7) were filled with the previously described I.B./lactose powder blend, closed and locked, and then extracted at 35° C. by the pressure swing extraction method. Drug and carrier FPM and retention in both extracted capsules as well as their corresponding control-filled capsules were then determined. Because lubricant is extracted in the presence of the drug powder, some extracted lubricant may partition between the powder phase and the supercritical phase inside the capsule. Lubricant adsorption on the powder is expected to induce particle agglomeration and thereby reduce FPM if it is not removed completely during the extraction process. Hence, the extraction may need to be conducted for a longer period of time to ascertain complete extraction of the lubricant from the capsule and the powder.

Table 9 depicts the retention and FPM of powder in these capsules. In general, powder retention, especially carrier retention, is lower in extracted capsules than in control capsules. Except for capsule lot 1 where FPM was slightly reduced by the extraction process, FPM is either unchanged or enhanced by the extraction demonstrating that lubricant was extracted from the locked capsules. For the combined lots, drug FPM in untreated capsules amounted to 16.0 μg while that in extracted capsules amounted to 17.1 μg. Drug retention in either untreated or extracted capsules is low and essentially equal (4.3 and 4.4 μg respectively). This study thus demonstrates that lubricant in locked and capsules can be extracted by SFE to produce formulations with generally higher and low powder retention.

TABLE 9

SFE of Filled Capsules: Effect on Drug and Carrier Retention and FPM
Lactose lot 2 and Drug Lot 1 Were Mixed to Form the Drug Powder

| Capsule Lot | Drug FPM (μg/caps) | Drug Retention (μg/caps) | Carrier FPM (μg/caps) | Carrier Retention (μg/caps) |
|---|---|---|---|---|
| 6 | 15.1 | 4.7 | 208.4 | 122.1 |
| e6 | 14.7 | 4.6 | 182.7 | 97.0 |
| 1 | 15.5 | 5.6 | 201.4 | 186.4 |
| e1 | 13.6 | 6.1 | 159.1 | 66.6 |
| 5 | 14.3 | 5.5 | 201.3 | 142.3 |
| e5 | 18.5 | 4.4 | 237.8 | 113.3 |
| 7 | 19.1 | 2.5 | 256.0 | 77.6 |
| e7 | 21.7 | 2.4 | 263.6 | 97.6 | u: Untreated; e: Extracted

Note that carrier retention in untreated capsules is much higher than carrier retention in extracted capsules (132.1 μg Vs 93.6 μg). This suggests that extracted lubricant attaches preferentially on drug particles which would then have a higher tendency to stick to the capsule walls during inhalation. Indeed, I.B. is a basic substance and is expected to interact more strongly with the extracted stearic acid and fatty acids present in the lubricant. This observation also explains why drug retention in extracted capsules is not substantially lower than in untreated capsules despite lubricant removal from the capsules. Lactose is an acidic substance and is therefore not expected to interact as strongly as I.B. with the extracted lubricant material.

Lubricant extraction from capsules by SFE methods was demonstrated. The methods can be used to extract lubricant material from either open capsules, closed capsules, locked capsules, or locked and filled capsules with no apparent physical or chemical damage to the capsules. Lubricant extraction has been shown to reduce drug and carrier retention, to increase drug FPM, and to improve reproducibility in either retention or FPM. The methods have also been shown to be useful in the extraction of moisture or other impurities from capsules, drug or carrier.

The SFE extraction of either closed capsules, open capsules, locked capsules, carrier or drug can be conducted at conditions where the temperature is in the range of 0.6–1.4 $T_c$, where $T_c$ is the critical temperature in K, and the pressure is in the range of 0.5–100 $P_c$. Hence, the SCF in either its subcritical or supercritical form may be used. Extraction may also be conducted in a direct manner; by mixing the vessel content while contacting the material to be extracted with the SCF; by fluidizing the material to be extracted with the SCF; or by pressure swing SFE. Preferably, the extraction is conducted within a temperature range of 1.0–1.1 $T_c$, and a pressure in the range of 1–10 $P_c$. In the case of extraction with $CO_2$, conditions of 31–90° C. and 1,070–10,000 psig are preferred. Also, either $CO_2$ or any other suitable SCF may be used, including hexafluorosullur, nitrous oxide, trifluoromethane, ethane, ethylene, propane, butane, isobutane, and mixtures thereof. Organic solvent modifiers may also be added to any of the SCFs to modify their solvent properties, including ethanol, methanol, acetone, propanol, isopropanol, dichloromethane, ethyl acetate, dimethyl sulfoxide, and mixtures thereof. Organic modifiers are used preferably at relatively low concentrations (0–20%). Similarly, light gases such as $N_2$, $O_2$, He, air, $H_2$, $CH_4$ and mixtures thereof may also be added in various proportions to the SCF to alter its extraction and transport properties

What is claimed is:

1. A method for removing supercritical fluid soluble material from the interior of a body or a cap or both of a hard shell capsule which comprises the steps of exposing the body or the cap or both of the hard shell capsule to a supercritical fluid which supercritical fluid has a critical temperature less than about 200° C. and a critical pressure of less than about 10,000 psi to transfer the supercritical fluid soluble material to the supercritical fluid and removing the supercritical fluid and the supercritical fluid soluble material from the body or the cap or both of the hard shell capsule.

2. The method as recited in claim 1 wherein the temperature is in the range of about 0.6 to about 1.4 $T_c$, where $T_c$ is the critical temperature in K and the pressure is in the range of about 0.1 to about 100 $P_c$, where $P_c$ is the critical pressure.

3. The method as recited in claim 1 wherein the cap of the hard shell capsule is placed over the open end of the body of the hard shell capsule.

4. The method as recited in claim 3 wherein the hard shell capsule further comprises a free-flowing powder within the body of the hard shell capsule.

5. The method as recited in claim 4 wherein the free-flowing powder comprises a pharmaceutical formulation.

6. The method as recited in claim 5 wherein the pharmaceutical formulation is for inhalation.

7. The method as recited in claim 6 wherein the pharmaceutical formulation for inhalation comprises ipratropium bromide, tiotropium bromide, oxytropium bromide, albuterol, albuterol sulfate, clenbuterol, fenoterol, beclomethasone diproprionate, glucose or lactose.

8. The method as recited in claim 1 wherein the supercritical fluid soluble material is mould lubricant.

9. The method as recited in claim 1 wherein the supercritical fluid comprises carbon dioxide.

10. The method as recited in claim 1 wherein the supercritical fluid comprises carbon dioxide and one or more organic solvents.

11. A method for removing supercritical fluid soluble material from the interior of a closed hard shell capsule which comprises the steps of exposing the closed hard shell capsule to a supercritical fluid which supercritical fluid has a critical temperature less than about 200° C. and a critical pressure of less than about 10,000 psi to transfer the supercritical fluid soluble material to the supercritical fluid and removing the supercritical fluid and the supercritical fluid soluble material from the closed hard shell capsule.

12. The method as recited in claim 11 further comprising periodically decreasing and increasing the pressure under which the closed hard shell capsule is exposed to the supercritical fluid.

13. The method as recited in claim 11 wherein the hard shell capsule further comprises a free-flowing powder within the interior of the hard shell capsule.

14. The method as recited in claim 13 wherein the free-flowing powder comprises a pharmaceutical formulation.

15. The method as recited claim 14 wherein the pharmaceutical formulation is for inhalation.

16. The method as recited in claim 15 wherein the pharmaceutical formulation for inhalation comprising ipratropium bromide, tiotropium bromide, oxytropium bromide, albuterol, albuterol sulfate, clenbuterol, fenoterol, beclomethasone dipropionate, glucose or lactose.

17. The method as recited in claim 12 wherein the supercritical fluid soluble material is mould lubricant.

18. The method as recited in claim 12 wherein the supercritical fluid is carbon dioxide.

19. A hard shell capsule wherein the body, the cap or both of such capsule has been exposed to a supercritical fluid to remove any supercritical fluid soluble material from the interior of such body, cap or both, wherein the supercritical fluid has a critical temperature less than about 200° C. and a critical pressure of less than about 10,000 psi.

20. The hard shell capsule as recited in claim 19 made from gelatin, cellulose, plastic or a blend of such materials.

21. The hard shell capsule as recited in claim 19 wherein the supercritical fluid soluble material is mould lubricant.

* * * * *